(12) United States Patent
Kumar et al.

(10) Patent No.: US 6,485,950 B1
(45) Date of Patent: Nov. 26, 2002

(54) ISOZYME OF AUTOCLAVABLE SUPEROXIDE DISMUTASE (SOD), A PROCESS FOR THE IDENTIFICATION AND EXTRACTION OF THE SOD IN COSMETIC, FOOD AND PHARMACEUTICAL COMPOSITIONS

(75) Inventors: Sanjay Kumar, Himachal Pradesh (IN); Rashmita Sahoo, Himachal Pradesh (IN); Paramvir Singh Ahuja, Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/617,118

(22) Filed: Jul. 14, 2000

(51) Int. Cl.$^7$ .............................. C12N 9/02; C12N 9/00; A61K 38/44
(52) U.S. Cl. ........................ 435/189; 435/183; 424/94.4
(58) Field of Search .................................. 435/189, 183; 424/94.4

(56) References Cited

U.S. PATENT DOCUMENTS 4,563,349 A * 1/1986 Miyata et al.
5,536,654 A * 7/1996 Gudin et al.

OTHER PUBLICATIONS

Beuno et al. Peroxisomal copper, zinc super oxide dismutase, characterization of the isoenzyme from watermelon cotyledons (1995) Plant Physiol., vol. 108, pp. 1151–1160.*

Gupta et al., Increased resistance to oxidative stress in transgenic plants that overexpress chloroplastic Cu/Zn superoxide dismutase (1993) PNAS, USA, vol. 90, pp. 1629–1633.*

* cited by examiner

Primary Examiner—Jon P. Weber
(74) Attorney, Agent, or Firm—Foley & Lardner

(57) ABSTRACT

The invention relates to a novel purified isozyme of an autoclavable superoxide dismutase extracted from the plant *Potentilla atrosanguinea Lodd.* Var. *orgyrophylla*, said isozyme having the following characteristics, $O_2^-$ scavenging activity remains same before and after autoclaving; scavenges $O_2^-$ from sub-zero temperature of $-20°$ C. to high temperature of $+80°$ C.; $O_2^-$ scavenging activity at $25°$ C. for 30 days without adding any stabilizing agent such as polyols or sugars; $O_2^-$ scavenging activity in the presence of saline (0.9% sodium chloride) to 61.8% of the control (without 0.9% sodium chloride), stable at $4°$ C. for at least 8 months; contamination free and infection free from any living micro- and/or macro-organism after autoclaving; possesses temperature optima at $0°$ C.; possesses a molecular weight of 33 kD under non-denaturating conditions; possesses a molecular weight of 36 kD under denaturating conditions; has clear peaks in UV range at 268 and 275 nm; has an enzyme turnover number of $19.53 \times 10^4$% per nmol per min at $0°$ C.; and requires Cu/Zn as a co-factor, method for the preparation of the purified isozyme of autoclavable superoxide dismutase and formulations containing the said autoclavable superoxide dismutase.

67 Claims, 12 Drawing Sheets

← TARGET ISOZYME

← Purified isozyme

NON-AUTOCLAVED   AUTOCLAVED

← Antigen-antibdy hybridization signal

ISOZYME OF AUTOCLAVABLE SUPEROXIDE DISMUTASE (SOD), A PROCESS FOR THE IDENTIFICATION AND EXTRACTION OF THE SOD IN COSMETIC, FOOD AND PHARMACEUTICAL COMPOSITIONS

FIELD OF INVENTION

The present invention relates to a novel purified isozyme of an autoclavable superoxide dismutase (EC 1.15.1.1; hereinafter, referred to "SOD"), a process for the identification and extraction of the said superoxide dismutase from *Potentilla astrisanguinea Lodd.* variety *argyrophylla* (Wall. ex. Lehm) Griers (hereinafter, referred to Potentilla) belonging to family Rosaceae. The invention also relates to a process for the extraction of the said SOD and its use in preparing many cosmetic, pharmaceutical and food compositions.

BACKGROUND AND PRIOR ART REFERENCES TO THE INVENTION

SOD is present in plant and animal cells to protect the cellular components against the deleterious effects caused by superoxide radical (hereinafter, referred to $O_2^{-\cdot}$). SOD dismutates superoxide radical into hydrogen peroxide and oxygen as per the following chemical reaction:

$$2\ O_2^{-\cdot} + 2\ H^+ = H_2O_2 + O_2$$

If $O_2^{-\cdot}$ is not removed, it reacts with $H_2O_2$ to produce a highly reactive hyroxyl free radical, which causes lipid peroxidation, protein denaturation and DNA mutation. A living system is said to be under oxidative stress, when such active oxygen mediated reactions are not being taken care of by enzyme systems.

SOD is a critical enzyme to manage oxidative stress both in plants and animal systems. Depending upon the co-factor requirements, the SOD can be Mn-SOD (SOD requiring manganese as a co-factor; localised in mitochondria; insensitive to potassium cyanide and hydrogen peroxide), Cu/Zn-SOD (SOD requiring copper and zinc as co-factors; localised in cytoplasm and chloroplast; sensitive to potassium cyanide and hydrogen peroxide) and Fe-SOD (SOD requiring iron as a co-factor; detected in microbes, blue-green algae and in a few species of higher plants).

SOD is also an important enzyme identified for imparting chilling tolerance to the plants and in stresses for example, water stress, low temperature stress, light stress (particularly, high light intensity), salt stress, radiation stress and all other stresses wherein $O_2^{-\cdot}$ is generated in excess quantity to damage the system (Foyer, C. H., Descourvieres, P. and Kunert, K. J. 1994. Plant Cell Environ. 17: 507–523; Allen, R. D., 1995. Plant Physiol. 107: 1049–1054).

In pharmaceutical applications, the enzyme has implications in all those diseases wherein $O_2^{-\cdot}$ is produced in a quantity so as to cause damage to the system. Hence, SOD in animal system has following implications:

(1) anti-inflammatory agent in wounds, burns etc. (Nimrod, A. Ezov, N., Parizada, L., Weiss, L., Tochner, Z., Slavin, S., Panet, A. and Gorecki, M. In Frontiers of Reactive Oxygen Species in Biology and Medicine (Eds. Asada, K. and Yoshikawa, T.) Excerpta Medica, Amsterdam, 1994, pp. 383–387);

(2) suppressors of asthamatic response (Ihaku, D., Tanimukai, T., Kitada, O., Taniguchi, N., and Sugita. M. In Frontiers of Reactive Oxygen Species in Biology and Medicine (Eds. Asada, K. and Yoshikawa, T.) Excerpta Medica, Amsterdam, 1994, pp. 407–408);

(3) suppressors of side-effects of anti-cancerous agents and in enhancing the life of tumor-bearing animals (Fugimoto, J. In Frontiers of Reactive Oxygen Species in Biology and Medicine (Eds. Asada, K. and Yoshikawa, T.) Excerpta Medica, Amsterdam, 1994, pp. 411–412);

(4) in relieving rheumatoid arthritis, SOD as a drug is administrated intra-articularly (Goebel, K. M. and Storck, U. 1983. Am. J. Med. 74: 124–128).

(5) in reducing the harmful effects of treatment with ionizing radiations (Edsmyr, F., Huber, W. and Menander, K. B. 1976. Curr. Ther. Res. Clin. Exp. 19: 198–211);

(6) in conferring cardiac protection during heart surgery, heart transplantation, kidney transplantation, and during transplantation of other organs such as skin, lung, liver, and pancreas (mentioned in Marklund; Stefan; Edlund; Thomas, 1998. U.S. Pat. No. 5,788,961);

(7) in prolonging the survival of the perfused isolated rabbit cornea (Neuwirth, L. O., and Dikstein, S. 1985. Curr. Eye. Res. 4: 153–154);

(8) in protecting the isolated lens against photoperoxidation (Varma, S. D. 1982. Ophthalmic Res. 14: 167–175);

(9) injection of SOD is helpful in reducing the frequency of intraventricular brain hemorrhage following hypotension (Ment, L. R., Stewart, W. B., and Duncan, C. C. 1984. J. Neurosurg. 62: 563–569);

(10) in ameliorating hepatitis in rats induced by injection of *Corynebacterium parvum* (Arthur, M. J., Bentley, I. S., Tanner, A. R., Saunders, P. K., Milluard-Sadlor, G. H., and Wright, R. 1985. Gastroenterology, 89: 1114–1122);

(11) in protecting kidneys against acute pyelonephritis (Robert, J. A., Roth, J. K. Jr., Domingue, G., Lewis, R. W., Kaack, B., Baskin, G. 1982. J. Urology, 128: 1394–1400) and nephrotoxic nephritis in rats (Rehan., A., Johnson, K. J., Wiggin, R. C., Kunkel, R. G. and Ward, P. A.1984. Lab. Invest. 51: 396–403);

(12) in ameliorating the functional and morphological abnormalities caused because of high blood pressure (Kontos, H. A. 1985. Circ. Res. 57: 508–516);

(13) in protection against diabetes mellitus and diabetogenic activity of alloxan (Grankvist, K., Marklund, S., Sehlin, J. and Taljedal, I. B. 1979. Biochem J. 782: 17–24.);

(14) in protection of tracheal cells against asbestos (Mossman, B. T., and Landesman, J. M. 1983. Chest, 835: 50s–51s);

(15) in relieving the depressor effect of spinal cord injury (Taoka, Y., Urakado, M., Koyanagi, E., Naruo, M., Inoue, M. In Frontiers of Reactive Oxygen Species in Biology and Medicine (Eds. Asada, K. and Yoshikawa, T.) Excerpta Medica, Amsterdam, pp. 241–242).

When SOD is to be injected in the body, a sterile composition would be needed and for that an autoclavable SOD would be an ideal one. Moreover, in reperfusion applications and storage of organs at low temperature, an autoclavable SOD would be required which can function efficiently at low temperature as well. Apart from the use of autoclaved SOD in pharmaceuticals and medical fields, sterile SOD will also be a choice in the cosmetic and food industry (for preventing oxygen disorders) as well.

(a) A number of formulations have been developed for pharmaceutical and cosmetic applications using SOD as one of the important antioxidant ingredients to scavange oxy free radicals from the system where applied. Availability of a SOD with autoclavability to ensure a germ free sterile preparation [the maximum thermostability of SOD described so far is at 80° C. (Gudin; Claude; Trezzy; Claudine 1996. U.S. Pat. No. 5,536,654); Bonaccorsi di Patti, M. C., Giartosio, A., Musci, G., Carlini, P. and Calabrese, L. (In Frontiers of Reactive Oxygen Species in Biology and Medicine. 1994. (Eds. Asada, K. and Yoshikawa, T.), Excerpta Medica, Amsterdam, pp. 129–130)], stability without adding an external stabilizer [the addition of hydrogen peroxide trapping agent, polyols, and sugars etc. are required to stabilise the enzyme from other sources such as germinated plant seeds (Bresson-Rival; Delphine; Boivin; Patrick; Linden; Guy; Perrier; Erric; Humbert; Gerard; 1999; U.S. Pat. No. 5,904,921)] and a wide range of temperature functionality from sub-zero to above 50° C. temperature [temperature range for SOD activity has been reported between 5 to 45° C. most of the workers (Burke, J. J. and Oliver, M. J. (Plant Physiol. 1992. 100: 1595–1598); Hakam, N. and Simon, J. P. (Physiol. Plant. 1996. 97: 209–216)] would immensely enhance the utility of the formulations and be more safe for use for humans.

The formulations/compositions mentioned below, but not limited to those mentioned below, have included SOD as one of the active ingredients:

(a) Hersh, T. in U.S. Pat. No. 5,922 dated Jul. 13, 1999 disclosed a composition for ameliorating free radical damage induced by tobacco products and environmental pollutants. The composition included, as active ingredients, reduced glutathione (0.5 mg) and a source of selenium (5 $\mu$g) selected from the group consisting of elemental selenium, selenomethionine and selenocysteine. The active ingredients were combined with suitable carriers and flavorings for their intraoral administration in concentrations for reducing free radical damage induced by tobacco products and other environmental pollutants to the oral cavity, pharynx and upper respiratory tract of a user and secondary smokers. Other antioxidants which were included in gels, lozenges, tablets and gums, the know-how for making these are well known to those engaged in such industry, consisted of vitamin C as ascorbic acid or as a derivative of ascorbic acid, vitamin E as alpha-tocopherol, SOD, vitamin A, beta-carotene, at least one amino acid selected from the group consisting of cysteine, methionin, taurine and arginine, a zinc salt such as zinc gluconate. The gum includes a gum base comprising approximately 40 to 60% by weight of the gum composition, wherein gum base comprises an elastomer, a polyvinyl acetate polymer, an acetylated monoglyceride, a wax with melting point below approximately 60° C. , an elastomer solvent, a plasticizer and a filler. The sweetener included in the gums was selected from the group consisting of xylitol, lactitol, sucrose, lactose and a saccharide. A lozenge comprised of a suitable carrier to enable the lozenge to slowly dissolve in a user's mouth releasing said active ingredients in concentrations for reducing free radical damage. The preparation reported in this patent are to be consumed by human being orally for reducing free radical damage induced by tobacco products and other environmental pollutants to the oral cavity, pharynx and upper respiratory tract of a user and secondary smokers. A germ free sterile preparation (because of autoclavability of SOD) will ensure no further infection to the smoker/secondary smoker to the affected portion.

(b) U.S. Pat. No. 5,904,921, discloses an anti-free radical cosmetic composition for anti-age, anti-wrinkles and anti-stress of skins. The composition was inclusive of SOD along with peroxidase with a peroxidase specific reducing substrate. The SOD was obtained from germinated seeds of barley, soya, wheat and peas, whereas peroxidase was obtained from black radish (or horseradish peroxidase) that was combined with an enzymatic substrate constituted by uric acid. Apart from horseradish peroxidases, the other groups of peroxidases included lactoperoxidase, glutathione peroxidase and spinal cord peroxidase. Similarly, the other groups of peroxidase substrates were glutathione, phenol, guaiacol, mesitol, 3,5-dichloro-2-hydroxybenzenesulfonic acid, aniline, dihydroxymaleic acid, cytochrome C, phenolphthalein, ascorbic acid, an iodide, a chloride, a bromide, 2–2'-azido-di(3-ethylbenzo-thiazoline-6-sulfonic acid, and SCN. The composition also included a lipophilic antioxidant such as tocopherol, tocopherol acetate, tocopherol linoleate, tocopherol phosphate in an effective antioxidizing amount. The composition comprising of SOD/peroxidase/peroxidase substrate (5%) was prepared in the form of a cosmetic emulsion which included: steareth-2 (3%), steareth-21 (2%), propylene glycol-15 stearyl ether (9%), cetearyl alcohol (2.5%), butylene alcohol (4.5%), water (73%), preservative comprising of parabens and phenoxyethanol (0.55), tocopherol (0.2%). Inventors used polyols, sugars to stabilize SOD at a temperature of at least 45° C.

(c) Another U.S. Pat. No. 6,011,067 issued on Jan. 4, 2000 by Hersh, T. teaches an antioxidant composition for the treatment of psoriasis, seborrhoeic dermatitis and related skin and scalp conditions. The said composition comprised L-glutathione (0.001% to 15% by weight) and selenomethionine a source of selenium in a suitable carrier for topical application. The composition further included zinc pyrithione, N-acetyl-L-cysteine, SOD, zinc oxide, zinc pyrithione, vitamin E, and vitamin C. The composition is encapsulated in protective membranes consisting of liposomes, nanospheres and glycospheres. The suitable carrier was in the form, but not limited to, of a member selected from the group consisting of a solutions, lotions, creams, oils, gels, sticks, sprays, ointments, balms, shampoo and pastes. The cream consisted of L-glutathione (reduced, 0.20%, L-selenomethionine (0.05%), N-acetyl-L-cysteine (0.25%), A,C,E Liposome (2.50%), Superoxide dismutase (0.25%) and Zinc pyrithione (0.25%). The spray also consisted to these active ingredients. The active ingredients in shampoo included L-glutathione (reduced, 0.20%, L-selenomethionine (0.025%), N-acetyl-L-cysteine (0.25%), A,C,E Liposome (2.00%), SOD (0.10%), Dex panthenol (0.5%) and Zinc pyrithione (1.0%). Inventor also described the use of pharmaceutically-acceptable aqueous or organic solvents (i.e. a solvent which is capable of having dispersed or dissolved therein the active compound, and possesses acceptable safety properties e.g., irritation and sensitization characteristics; in amounts ranging from 0.1% to 99% and preferably from 2.0% to 75%) as suitable topical compositions. Such solvents can be water, 1,2,4-butanetriol, propylene glycol, sorbitol esters, butylene glycol, polyethylene glycol, polypropylene glycol, glycerol, 1,2, 6-hexanetriol, ethanol, isopropanol, butanediol and mixtures thereof (d) U.S. Pat. No. 5,296,500 discusses formulations as an aerosol to be applied to the skin as a spray and topical pharmaceutical compositions as an pharmaceutically acceptable emollient (materials used for the prevention or relief of dryness, as well as for the protection of the skin). The formulations as aerosol require a propellant to be added to a solution composition. Examples of useful propellants included, but not limited to, the chlorinated, fluorinated and chloro-fluorinated lower molecular weight hydrocarbons.

Further, U.S. Pat. No. 5,470,876 discloses the use of SOD as a topical anti-alopecia agent compounded in a topical formulation. The pharmaceutical carriers for dispersion of SOD which were mentioned included water, urea, alcohols and glycols such as methanol, ethanol, propanol, butanol, ethylene glycol, propylene glycol, and the like. Suitable water-in-oil emulsions that are commercially available were also mentioned which included Aquaphor, cold cream, Eucerin, hydrous lanolin, Hydrosorb hydrophilic petrolatum, Nivea, Polysorb, Qualatum and Velvachol. Suitable oil-in-water emulsions that are commercially available were also mentioned and it included acid mantle cream, Almay emulsion cream, Cetaphil, Dermabase, Dermavan, hydrophilic ointment, Keri cream, Lubriderm cream, Multi base cream, Neobase cream, Unibase cream, Vanibase cream and Wibi. The carrier described contained various other emollients, emulsifiers, water, perfumes, colorants, preservatives, and the like. The topical formulation mentioned was in the form of a cream, lotion, shampoo, cream rinse, or the like. Inventor selected SOD active compound from one or more of copper salicylate, copper aspirinate, indomethacin-copper and a complex of an amino acid or peptide and a transition metal. The amino acid was selected from one or more of glycine, histidine, lysine, arginine, cysteine and methionine, and the metal was selected from one or more of copper, iron, zinc and manganese. The peptide consisted of glycine, histidine, lysine, arginine, cysteine or methionine. The peptide was selected from one or more of histidyl lysine, glycyl histidine, glycyl hystidyl lysine and lysyl histidyl lysine. Thus various formulations included: (a) addition of 500 mg of copper salicylate (source of SOD active compound) to a commercially available non-medicated shampoo, and allowing the mixture to dissolve for 2–3 days; (b) copper salicylate (source of SOD active compound) was suspended in deionized water at 1 g/100 ml; (c) mixing together Water(1600 ml), Spironolactone (100 g), Copper Salicylate (50 g), BHT (50 g), Ascorbyl Palmitate (50 g), Minoxidil (1.2 g), Phenytoin (50 g), Tretinoin (2 g), Arginine (50 g) The mixture was then blended together with 900 ml of dimethylsulfoxide and 4.08 kg of Dermovan cream vehicle to make a lotion; (d) a lotion was made by homogenizing the ingredients: Copper aspirinate, (0.1 g), Ascorbyl palmitate (0.5 g), Dermovan emulsion (100 g); (e) another lotion was made by homogenizing the ingredients: Lysyl-histidyl-lysine (50 mg), Cupric chloride (50 mg), Spironolactone (0.5 g), Water (30 ml), Propylene glycol (30 ml), Ethanol (20 ml); (f) yet another lotion comprised glycyl-(L)-histdyl-(L)-lysyl-(L)-valyl-(L)-phenylalanyl-(L)-valine and the metal comprises copper (II). The ratio of peptide to metal ion in the complex was 2:1. The ingredients were homogenized into a topical lotion in the proportions: peptide:Cu complex (1% wt/wt), Nonoxynol-9 (5%) and Unibase cream (94%).

(e) U.S. Pat. No. 5,925,363 used SOD in combination with melanin pigments in a cosmetic, hygienic or pharmaceutical compositions to be employed topically to combat cutaneous aging and to protect the skin against the effects of the free radicals induced, for example, by atmospheric pollutants and/or by ultraviolet radiation. composition was also intended to protect the hair and mucosa against the effects of the free radicals. Some of the formulations used were as follows: (a) formulation for oil-in-water emulsion included: SOD (sold by the company Pentapharm q.s. 600 units (19 g), melanin pigment obtained by oxidizing polymerization of 5,6-dihydroxyindole in the presence of aqueous hydrogen peroxide and aqueous ammonia (0.05 g), polyethylene glycol polyoxyethylenated with 50 moles of ethylene oxide (1.5 g), diglyceryl monostearate (1.5 g), liquid paraffin (24 g), cetyl alcohol (2.5 g), triethanolamine q.s. pH 7, Water q.s. (100 g); (b) the second formulation was water in oil emulsion and it included: SOD (sold by the company Bio-Technologie 0.00012 g q.s. 1,000 units), melanin pigment (0.1 g), pigments (iron oxides) (0.5 g), polyglyceryl sesquiisostearate (4 g), white beeswax (0.5 g), magnesium stearate (1.5 g), aluminum stearate (1 g), polyoxyethylenated hydrogenated castor oil with 7 moles of ethylene oxide (3 g), isopropyl palmitate (10 g), perhydrosqualene (15 g), water q.s.(100 g). Inventors described other formulations and enormous sources of SOD, and various types of SOD. Dermopharmaceutical formulations, apart from the SOD and melanin and active ingredient, mentioned in the patent included surfactants, colorants, perfumes, preserving agents, emulsifiers, liquid carriers such as water, fatty substances intended to form the fatty phase of emulsions (such as milks or creams), resins and the like. The compounds intended to form a fatty phase were, for example, mineral or organic, vegetable or synthetic oils, waxes, fatty alcohols or fatty acids. Liquid paraffin was mentioned, for example, among inorganic oils and, among synthetic oils, ethyl and isopropyl palmitates, alkyl myristates such as isopropyl, butyl or cetyl myristate, hexyl stearate, triglycerides of octanoic and decanoic acids, cetyl ricinoleate, stearyl octanoate (purcellin oil) and hydroxylated polyisobutene octanoate. Among the vegetable oils was mentioned, for example, sweet almond oil, avocado oil, coconut oil, wheatgerm oil, corn oil, castor oil, olive oil, palm oil, sesame oil, soya oil, argan oil, evening primrose oil, borage oil, essential oils and vegetable waxes such as beeswax or else synthetic waxes such as silicone waxes. Among fatty alcohols was mentioned, cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol, erucyl alcohol and 2-octyl-dodecanol. Among the fatty acids there was mention of stearic acid, myristic acid, palmitic acid, oleic acid, linoleic acid, lauric acid, isostearic acid, hydroxy-stearic acid, linolenic acid, ricinoleic acid, arachidic acid, behenic acid, erucic acid and lanolinic acids. The compositions which were intended for a topical application were especially solutions or dispersions of the lotion or serum type, emulsions of liquid or semiliquid consistency of the milk type, which are obtained by dispersing a fatty phase in an aqueous phase (oil in water) or vice versa (water in oil) or suspensions or emulsions of soft consistency of the cream or gel type, or else microgranulates, or vesicular dispersions of ionic and/ or nonionic type. The compositions were arranged in an appropriate container which is itself optionally arranged in an individual package. These compositions were prepared by the usual methods. They form especially cleansing creams for protecting or care of the face, the hands or the body (for example day creams, night creams, makeup removal creams, foundation creams, sun creams), fluid foundations, makeup removal milks, body protection or care milks, sun milks, lotions, gels or mousses for skin care, such as cleansing lotions, sun lotions, artificial tanning lotions, compositions for the bath or deodorizing compositions containing a bactericidal agent. The compositions could also consist of solid preparations forming soaps or cleansing cakes. The compositions could also be packaged in the form of an aerosol composition also containing a pressurized propellant agent. The compositions for hair could be presented in the form of aqueous, alcoholic or hydroalcoholic solutions or in the form of creams, gels, emulsions, mousses or else in the form of an aerosol composition also containing a pressurized propellant agent. Besides the conventional active ingredients various adjuvants were also mentioned that are usually present in these compositions for hair, for example liquid or gel-form carriers, perfumes, dyes, preserving agents, thickening agents and the like. Inventors mentioned that the synergistic combination of SOD and melanin could be incorporated as a main or secondary ingredient, in various compositions for hair care forming, for example, creams, lotions, gels, serums or mousses for the care of the scalp, shampoos, hairsetting lotions, treating lotions, styling creams or gels, dye compositions (especially oxidation dyes) optionally in the form of dyeing shampoos, restructuring lotions for hair, permanent wave compositions (especially compositions for the first step of a permanent waving), lotions or gels to combat hair loss, and the like. The compounds of the invention may be especially: shampoos containing, besides a SOD and the melanin pigments a cationic, anionic or nonionic detergent, dyeing compositions including coloring shampoos which contain dyes or usual dye precursors, compositions for the first step (reduction step) of a deformation of hair, containing reducing derivatives such as mercaptans, sulphites and the like, compositions for slowing down the loss of hair and for promoting fresh growth of hair, containing compounds such as minoxidil (2,4-diamino-6-piperidino-3-pyrimidine oxide) and its derivatives, diazoxide (7-chloro-3-methyl-1,2,4-benzothiadiazine, 1,1-dioxide) and phenytoin (5,5-diphenyl imidazolidine-2,4-dione). The cosmetic composition of the invention may also be for oral and dental use, for example a toothpaste. In this case the composition would contain usual adjuvants and additives for compositions for oral use and especially surface-active agents, thickening agents, moisturizers, polishing agents such as silica, various active ingredients such as fluorides, in particular sodium fluoride, and optionally sweetening agents such as sodium saccharinate. The cosmetic treatment was intended to be used in the form of creams, of gels, of serums, of lotions, of makeup removal milks or antisun compositions to the skin or to the hair, application of a hair lotion to wet hair, shampooing or application of toothpaste to the gums to obtain the desired protection effect. This cosmetic treatment process was intended in particular to maintain the keratinous structure of the skin or of the hair so as to avoid their degradation and the harmfull effects of such a degradation under the influence of the free radicals induced especially by atmospheric pollutants, to maintain or improve the characteristics of the skin (softness, suppleness, elasticity), of the hair or of the mucosa, to protect the skin or the hair against the harmful effects of ultraviolet rays and in particular to treat or prevent the premature aging of the skin.

(f) U.S. Pat. No. 5,137,820 teaches the use of medium/higher fatty acid glyceride for preparation of the composition for oral administration of SOD. Representative examples of such fatty acid glyceride include the mono-, di- and triglycerides of caprylic acid, capric acid, lauric acid, myristic acid, palmitic acid, oleic acid, linoleic acid, linolenic acid or the like. These fatty acid glycerides can be used singly or in combination. The fatty acid glyceride may be a naturally-occurring compound or a synthetic or semi-synthetic compound. The use of natural vegetable oil was also taught. The vegetable oils which can be employed with advantage include, among others, olive oil (oleic acid 70–80%, linolic acid 4–12%, palmitic acid 7–15%), maize oil (linolic acid 40–60%, palmitic acid 25–45%), sesame oil (oleic acid 35–46%, linolic acid 35–48%), camellia oil, coconut oil (lauric acid 45–52%, capric acid 4–12%, caprylic acid 6–10%) and palm oil. Commercial products can be used as such. Thus, for example, commercially available medium fatty acid triglycerides can be utilized. As for higher fatty acid triglyceride, commercial edible oils such as olive oil can be utilized. The aforesaid amphiphilic agent is a non-toxic agent having both hydrophilicity and lipophilicity. Typical examples of such amphiphilic agent that were mentioned included natural amphoteric surfactants, polyglycerin fatty acid ester, polyoxyethylene-sorbitan fatty acid ester (Tween series), sorbitan fatty acid ester (Span series) and polyethylene glycol. Preferred amphoteric surfactants are soybean phospholipid, yolk lecithin and their related substances, such as commercial phosphatidylcholine, yolk lecithin, soybean lecithin, phosphatidylethanolamine, etc. Aside from the above, anionic surfactants such as sodium laurylsulfate and cationic surfactants such as benzalkonium chloride, benzethonium chloride, etc. can also be employed. The alkanol to be included may for example be ethanol, propanol, isopropyl alcohol, butanol or the like. The proportion of said fatty acid glyceride is about 0.1 to 100 ml per mg of the SOD derivative and preferably about 0.5 to 5 ml on the same basis. The addition of said amphiphilic agent and/or lower alkanol was optional but these agents contributed to enhanced wettability with the oil and increased dispersibility or solubility therein so as to give a stable composition with an additional effect of enhanced absorption after oral administration. The proper level of addition of said amphiphilic agent varies with different species thereof. Generally, however, with respect to 1 mg of the SOD derivative, it is appropriate to employ 0.01 to 0.1 ml when the amphiphilic agent is a liquid or 0.05 to 5 mg when it is a solid agent. The level of addition of said lower alkanol may be about 1 to 15 weight percent based on the total weight of the composition. The addition of such lower alkanol leads to an improved homogeneity of the solution.

(g) U.S. Pat. No. 5,897,879 teaches a sustained-release pharmaceutical delivery system for the administration of an antioxidant drug to a patient in need of such drug to reduce increased formation of active oxygen species. The delivery system comprised antioxidant drug in combination with a polymeric matrix which does not interact with the antioxidant drug or a mixture of such polymers. Inventors mentioned a great variety of polymers that might be natural, modified natural or synthetic hydrophilic or hydrophobic polymers such as, for example gelatin, ovalbumin, soybean proteins, gum Arabic, modified starch, methylcellulose, hydroxypropyl cellulose, hydroxypropylmethyl cellulose and like polymers and mixtures thereof, or a hydrophobic polymer such as a polyamide, polyacrylate, polyurethane, waxes, polypropylene, ethyl cellulose and like polymers and mixtures thereof, or mixtures of such hydrophilic and hydrophobic polymers. Inventors mentioned the antioxidant drugs such as are various forms of vitamin E, such as alpha-d-tocopherol, alpha-dl-tocopherol, alpha-d-tocopherol acetate, alpha-dl-tocopherol acetate or alpha-d-tocopherol acid succinate, ascorbic acid, beta-caroten and selenium. The various formulations may be prepared by mixing the polymer or mixture of polymers with the active antioxidant drug, by methods as described in the following examples as well as by other methods known to the man versed in the art. Inventors mentioned that the delivery system of the present invention may be adapted to dosage forms for local, for example opthalmic, and transdermal administration, as well as implants which will release the active antioxidant drug in a controlled manner. Particular forms suitable for such administration include, for example, films. The film could be prepared from ethanolic or chloroformic solutions of the polymers. The drug was also released faster from films comprising polyethylene glycol. The amount of active antioxidant drug could vary as desired for a therapeutically effective amount and might depend on the patient's age, sex, weight, physical condition, disease or condition to be treated, and other medical criteria as well as on the relative efficacy of the drug. This effective amount may be determined by techniques known in the art. For example, in case the antioxidant drug is vitamin E, the amount of the drug is a dosage unit form may be from about 10 IU to about 1000 IU. The various dosage forms according to the invention may be prepared and tested by techniques will known in the art. Inventors mentioned that the delivery system might be used for treating various pathological conditions for example, various cancers (stomach, lung, colon), esophagal dysphasia, stroke, cataract, gastric mucosal injury, oral leukoplakia, Parkinson's disease and related neurological disorders, cardiac disorders and tardive dyskinesia. Administration of antioxidant drugs, enabled by the delivery system was also expected to increase the life span of the treated patient.

(h) U.S. Pat. No. 5,942,245 reveales the use of SOD in liposomes, optionally mixed with hyaluronic acid and/or at least one physiologically acceptable carrier, and other optional additives, to prepare a pharmaceutical composition useful against increased concentrations of superoxide radicals and/or the damage caused thereby. These compositions can be administered topically, orally and/or parenterally to prevent and/or heal burns, skin lesions due to radiation, inflammations, rheumatic and arthritic diseases, bronchitis, ARDS, emphysema, allergic oedemas and other inflammatory process, possibly trigged by microbial infections. They may also be used in the cosmetic treatment of furuncles, acne and the like. They may also be used to improve the preservability of organic, preferably biogenic, materials, in particular organ transplants and liquids with organic components, as well as foodstuffs.

(i) Another U.S. Pat. No. 5,827,886 reveales a composition and method of reducing the inflammation and pain of various clinical entities including, but not limited to, the arthritis of rheumatoid arthritis and the other so-called autoimmune diseases, and osteoarthritis, the common syndrome of low back pain, myalgias, neuropathies, such as that of diabetes, and neuralgias, such as after shingles (herpes) as well as any cutaneous manifestations, if any, of these conditions. In addition, the compositions deal with reduction of free radicals initiated by exercise of any form and amelioration of the post-exercise signs and symptoms of muscle strain and connective tissue alterations. The composition comprises an effective amount of the endogenous antioxidant, glutathione, in its reduced form and a selenoamino acid, such as selenemethionine or selenocysteine, which may act as both a selenium co-factor of the synergistic antioxidant glutathione peroxidase, and selenium as itself, an antioxidant. In addition, other intra and extracellular synergistic antioxidants of L-glutathione, namely, SOD, ascorbic acid (vitamin C), acetyl-L-carnitine and glutathione reductase, the latter provided in a thiol rich extract preparation, may be employed. The preparations described may be in the forms of creams, lotions, solutions including sprays and aerosols and in roll-on dispensing bottles, ointments, gels, balms, patches, or emulsions as are known in this industry. Other free radical scavengers, antioxidants, anti-inflammatory agents, and local anesthetics, particularly capsaicin, could be included in the composition to deal with the inflammation and chronic pain characteristic of these diseases and clinical syndromes. These included but are not limited to the anti-oxidants, tocopherols (vitamin E), green tea and pycnogenols and also steroids, nonsteroidal anti-inflammatories, capsaicin extract, tissue respiratory factor and the local anesthetics of the caine family.

(j) U.S. Pat. No. 5,875,798 reveales a method of treating oral and systemic diseases which included impregnating or coating a toothpick with active therapeutic agents and rubbing the toothpick against mouth tissue to release the active therapeutic agents onto the tissue for penetration through the tissue. The active therapeutic agent was selected from the group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate. An additional therapeutic agent may also be impregnated or coated on the toothpick, for example, antimicrobials, antibiotics, antioxidants, anti-plaque agents, analgesics, anti-tartar agents, anti-caries agents, hemostatic agents, anti-inflammatory agents, hormones, bleaching agents, vitamins, vaccines, caffeine and monoclonal antibodies. Since antioxidants enhance the healing of infected and noninfected wounds by reducing the damage caused by oxygen radicals, these include but are not limited to: vitamin E, pyruvate β-carotene, selenium, N-acetylcysteine, vitamin C, antioxyenzymes such as SOD, catalase, glutathione peroxidase, and glutathione reductase together with the enzymes of the pentose monophosphate shunt pathway that regenerate NADPH. Pyruvate is one of the few antioxidants that readily enter cells, making it an ideal cytoplasmic antioxidant. Pyruvate alone or in combination with alpha tocopherol, vitamin E, inhibits reactive oxygen-induced damage. Vitamin E, a term that encompasses a small group of related tocopherols, is the major lipid-soluble antioxidant responsible for protecting the polyunsaturated fatty acids in membranes against lipid peroxidation. Tocopherols protect lipids by scavenging peroxyl radicals precluding further chain propagating steps. Inventors mentioned the addition of other active components such as vitamin B-12 may be added to the toothpick to achieve the desired therapeutic effects.

Apart from the use of SOD in various pharmaceutical, cosmetic and food industry, the enzyme plays crucial roles in plant industry as well. Thus, for example, but not limited to, a SOD with lower temperature optima will aid in protecting the plant against oxidative stresss during winter months. And, a high thermal stability of the enzyme would be a desirable feature for the plant experiencing intense photoinhibition during hot summer and drought stress.

Given below is the state of art in relation to thermostability and temperature requirements for SOD functioning:

Reference may be made to a document by Burke, J. J. and Oliver, M. J. (Plant Physiol. 1992. 100: 1595–1598) wherein SOD is described to possess properties from pea (*Pisum sativum* L. var Progress No. 9) assayed at temperature varying between 10° C. to 45° C. Chloroplast localised Cu/Zn-SOD was found to have highest activity at 10C, whereas Mn-SOD and cytosolic Cu/Zn-SOD showed no change in activity between 10° C. -30° C. The enzyme activity was lowest at 45° C.

Reference may be made to another document by Hakam, N. and Simon, J. P. (Physiol. Plant. 1996. 97: 209—216) wherein is described SOD properties assayed at two temperatures of 5 and 25° C. from a $C_4$ grass *Echinochloa crus-galli* (L.) Beauv. No change in the enzyme activity was observed at these two temperatures.

Reference may be made to yet another document by Bonaccorsi di Patti, M. C., Giartosio, A., Musci, G., Carlini, P. and Calabrese, L. (In Frontiers of Reactive Oxygen Species in Biology and Medicine. 1994. (Eds. Asada, K. and Yoshikawa, T.), Excerpta Medica, Amsterdam, pp. 129–130) wherein thermostability of Cu/Zn-SOD has been analysed from ox, sheep, shark, yeast, and *Xenopus laevis* and showed conformational melting temperatures to be 88.05, 87.1, 84.1, 73.1 and 71.15° C., respectively. However, there was no mention of the enzyme activity at various temperatures. Also, the enzymes were reported to be denatured when heated beyond transition peak.

Another reference from Bueno P., Verla, J., Gallego, G. G., and Rio del A. L. (Plant Physiol. 1995. 108: 1151–1160) wherein the thermostability of Cu/Zn SOD isolated from the cotyledon of water melon has been shown, SOD activity reduced:

(a) by 40% after 4 hour of incubation at 50° C.;
(b) by 50% after 15 minute of incubation at 70° C.;
(c) by 80% after 60 minute of incubation at 80° C.; and
(d) by 100% after 15 minute of incubation at 100° C.

Reference may be made to Document by Miyata, K., Maejima, K., and Tomoda, K. (U.S. Pat. No. 4,563,349; Jan. 7,1986) wherein SOD has been reported from a microorganism belonging to genus Serratia having the thermostability characters as follows:

(a) Stable at 37° C. for 60 minutes;
(b) Inactivated by 50% when incubated at 50–60° C. for 60 minutes; and
(c) Inactivated by 100% when incubated at 80° for 5 minutes.

Reference may be made to Document by Gudin; Claude; Trezzy; Claudine (U.S. Pat. No. 5,536,654; Jul. 16, 1996) which describes the production and extraction of SOD from a photosynthetic microorganism culture, which is thermostable upto 80° C.

The drawbacks of the SOD as reported in the prior art are:

(a) There is no reported SOD which could be autoclaved, to ensure a germ free sterile preparation and, at the same time, can catalyze dismutation of $O_2^{-\cdot}$ at lower temperature. The maximum thermostability of SOD reported so far is at 80° C. (Gudin; Claude; Trezzy; Claudine 1996. U.S. Pat. No. 5,536,654) and the minimum temperature reported for catalyzing dismutation is 5° C. (Hakam, N. and Simon, J. P. 1996. Physiol. Plant. 97: 209–216). However, thermostability and lower temperature for catalyzing dismutation of $O_2^{-\cdot}$ are not reported for the same enzyme.

(b) There is no reported SOD which can catalyze dismutation of $O_2^{-\cdot}$ at sub-zero temperatures.

(c) Prior art procedures for carrying out enzyme assay do not describe any method to study activity at sub-zero temperatures.

(d) Prior art procedures do not describe the method to identify the isozymes encompassing unique properties of sub-zero and higher temperature functionality before the purification of the enzyme could be taken up.

(e) Reported SODs do not retain their activity at ambient temperature unless stabilized by the addition of polyols, sugars or any other stabilizing agent (Bresson-Rival;

Delphine; Boivin; Patrick; Linden; Guy; Perrier; Erric; Humbert; Gerard; 1999; U.S. Pat. No. 5,904,921).

(f) Prior art procedures for SOD purification do not ensure complete elimination of the associated proteins.

(g) Although there are several procedures for purification of SOD (Beaman, B. L.; Scates, S. M.; Moring, S. E.; Deem, R.; And Misra, H. P.; Journal of Biological Chemistry, 258: 91–96, 1983; Steinman, H. M.; Journal of Biological Chemistry, 257, 10283–10293) We have not encountered any reference wherein a particular isozyme of SOD has been targeted for the purpose of purification.

The above drawbacks have been eliminated for the first time in a simple, reliable and reproducible manner by the present invention, yielding outstanding results.

OBJECTS OF THE INVENTION

The main object of the present invention is to provide a novel purified isozyme of superoxide dismutase extracted from the plant *Potentilla astrisanguinea Lodd.* Var. areyrophylla.

Another object is to provide a novel purified isozyme of superoxide dismutase said isozyme capable of being autoclaved at temperature upto 121° C. to ensure a cheap germ-free sterile preparation for pharmaceuticals, cosmetics and food industry.

Another object of the present invention is to provide a SOD which can function efficiently at low temperatures (0° C.)—(−10° C.).

Still yet another object of the present invention is to provide SOD in which the feature of autoclavability and functioning at low temperature, is possessed by the same SOD.

Yet another object of the present invention is to provide a method to identify the isozyme which show the activity at temperatures higher that +50° C. and at sub-zero temperatures.

Another object of the present invention is to provide a process to purify an autoclavable SOD enzyme which can function between the temperatures ranging between +80 to −10° C.

Still another object of the present invention is to provide a SOD which can function at sub-zero temperatures.

Yet another object of the present invention is to provide a SOD which is stable at ambient temperature (25° C.) at least for one month without adding any stabilizing agent such as, but not limited to, polyols or sugars.

Yet another object of the present invention is to provide a process to assay SOD activity at sub-zero temperatures.

Yet another object of the present invention is to provide a process for more complete purification of SOD to eliminate the proteins carrying same charge but different molecular weight.

SUMMARY OF THE INVENTION

The present invention relates to the process for identification and the extraction of SOD from Potentilla which,
(a) is autoclavable at 121° C. under a pressure of 1.1 kg per square centimeter to ensure a germ free sterile SOD,
(b) is stable to boiling in distilled water for 1 hour, and
(c) has free radical scavenging capability ranging between sub-zero (−10° C.) to +80° C. Particularly, this invention describes the procedure to purify one of the isozymes of SOD showing the above mentioned properties from the plant Potentilla and can be used in medical, cosmetic and food industry/research, and also in producing transgenic plant resistance/tolerance to biotic and abiotic stresses in which, the damage is mediated through the production of $O_2^-$.

DETAILED DESCRIPTION OF THE INVENTION

Accordingly, the invention provides novel purified isozyme of an autoclavable superoxide dismutase extracted from the plant *Potentilla astrisanguinea Lodd.* Var. areyrophylla, said isozyme having the following characteristics:
(a) $O_2^-$ scavenging activity remains same before and after autoclaving;
(b) scavenges $O_2^-$ from sub-zero temperature of −20° C. to high temperature of +80° C.;
(c) $O_2^-$. scavenging activity at 25° C. for 30 days without adding any stabilizing agent such as polyols or sugars;
(d) $O_2^-$. scavenging activity in the presence of saline (0.9% sodium chloride) to 61.8% of the control (without 0.9% sodium chloride).
(e) stable at 4° C. for at least 12 months;
(f) contamination free and infection free from any living micro- and/ or macro-organism after autoclaving;
(g) possesses temperature optima at 0° C.;
(h) possesses a molecular weight of 33 kD under non-denaturating conditions;
(i) possesses a molecular weight of 36 kD under denaturating conditions;
(j) has clear peaks in UV range at 268 and 275 nm;
(k) has an enzyme turnover number of $19.53 \times 10^4$% per nmol per min at O° C.; and
(l) requires Cu/Zn as a co-factor.

Further, the invention provides a method for identification of the target isozyme of the superoxide dismutase said method comprising the steps of:
(a) localizing various isozymes of SOD in the crude extract of the leaf on 7–12% native polyacrylamide gel;
(b) after electrophoresis, rinsing the gel with distilled water followed by incubation for 30 minutes in 2.5 mM NBT;
(c) immersing the gel in $1.17 \times 10^{-6}$ M riboflavin for 20 minute and removed later onto a petri plate to expose to a light intensity of 25–1000 μ Einstein/m$^2$/second using a fiber optic light source (Nikon) to develop purple color throughout the gel except for the locations where SOD was localized;
(d) incubating with nitroblue tetrazolium and riboflavin, and exposing to light at 4 different temperatures of −20, 4, 25 and 60° C.;
(e) when working at −20° C., adding glycerol (50% final concentration) in the incubation solution to avoid freezing;
(f) identifying the most prominent isozyme at all the temperatures and selecting for the purpose of purification.

In an embodiment, the invention provides a method for the preparation of purified novel isozyme of SOD wherein the said method comprises the steps of:
a) homogenizing leaf tissue in a homogenizing buffer at pH 7.0–7.5 and at a temperature range between 4–8° C.;
b) filtering the homogenate and centrifuging the filtrate at 8,000–13,000 rpm for 10–30 minutes at 4–8° C.;
c) decanting the supernatant for purification of SOD;
d) precipitating SOD with 30–60% ammonium sulfate;
e) dissolving the precipitate in a 10 to 100 mM buffer at pH 7 to 7.5 and dialyzing for 18–36 hours with 6–12 changes of the buffer;
f) loading the dialyzed protein onto a DEAE-Cellulose column and eluted with 100 to 500 ml of 100–500 mM KCl prepared in a buffer (all autoclaved or non-autoclaved;
g) assaying fractions containing protein for SOD;
h) fractionating SOD containing fractions on a high pressure liquid chromatography using 100–200 mM KCl prepared in 10–50 mM phosphate buffer (all autoclaved or non-autoclaved) with a flow rate of 0.8–1.0 ml per minute;
i) assaying each peak was assayed for SOD activity. SOD peak, obtained after HPLC and concentrating using a protein concentrator column;
j) assaying concentrated protein for SOD activity at different temperatures ranging between −10 to +80° C. in the presence of glycerol to avoid freezing at sub-zero temperatures;

k) localizing the purified SOD on 7 to 12% polyacrylamide gel by known methods;

In yet another embodiment, the invention provides a method for the preparation of novel isozyme of SOD to facilitate enzyme assay at sub-zero temperatures In still another embodiment, the invention provides a method for the preparation of novel isozyme of SOD wherein the source of novel SOD may be selected from other high altitude plants species from Himalayan or similar regions.

In another embodiment, the invention provides a method where the source of novel SOD may be further selected from Aconitum sp., Artemisia sp., *Trigonella emodi, Hippophae rhamnoides, Hippophae tibetana, Arnaebia euchroma, Dactylorhiza hatagirea,* Aquilegia sp., Ranunculus sp., *Rosa webbiana,* Podophyllum sp., *Ephedra gerardiana, Caragana jubata, Geum elatum, Picrorhiza kurooa,* and other flora and micro flora, and fauna found at high altitude location would also yield novel SOD.

The invention also provides a formulation comprising a plant superoxide dismutase (SOD) in isozyme as an active ingredient, together with reduced glutathione, source of selenium, carriers, flavouring agents and oxidants.

The invention also provides a formulation comprising a plant superoxide dismutate (SOD) isozyme together with an effective amount of cosmetically acceptable peroxidase, cosmetically acceptable peroxidase cofactor, solvents, carriers and conventional additives The invention also provides a formulation comprising isozyme of SOD, along with antioxidants such as, but not limited to, L-glutathione (0.001% to 15% by weight) and selenomethionine a source of selenium in a suitable carrier for topical application for the treatment of psoriasis, seborrhoeic dermatitis and related skin and scalp conditions.

In yet another embodiment, the invention provides a formulation comprising plant superoxide dismutase (SOD) isozyme as claimed in claim 1 and capable of being used for topical application either as, but not limited to, solutions or dispersions of the lotion or serum type, emulsions of liquid or semiliquid consistency of the milk type, which are obtained by dispersing a fatty phase in an aqueous phase of oil-in-water or vice versa i.e. water-in-oil or suspensions-or emulsions of soft consistency of the cream or gel type, or else microgranulates, or vesicular dispersions of ionic and/or nonionic type.

In another embodiment, the invention provides a drug delivery system comprising purified isozyme of SOD together with antioxidant drug in combination with a polymeric matrix, which does not interact with the antioxidant drug or a mixture of such polymers.

Use of SOD for preparation of formulations involving SOD such as water-in-oil emulsions that are commercially available such as, but not limited to, Aquaphor, cold cream, Eucerin, hydrous lanolin, Hydrosorb, hydrophilic petrolatum, Nivea, Polysorb, Qualatum and Velvachol.

Use of SOD for preparation of formulations involving SOD such as oil-in-water emulsions selected from acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi.

Use of the isozyme of SOD for preparation of gels, lozenges, tablets and gums wherein the isozyme of SOD is mixed with gums, tablets to ensure a germ free sterile preparation.

BRIEF DESCRIPTION OF ACCOMPANYING DRAWINGS

Figure 1:
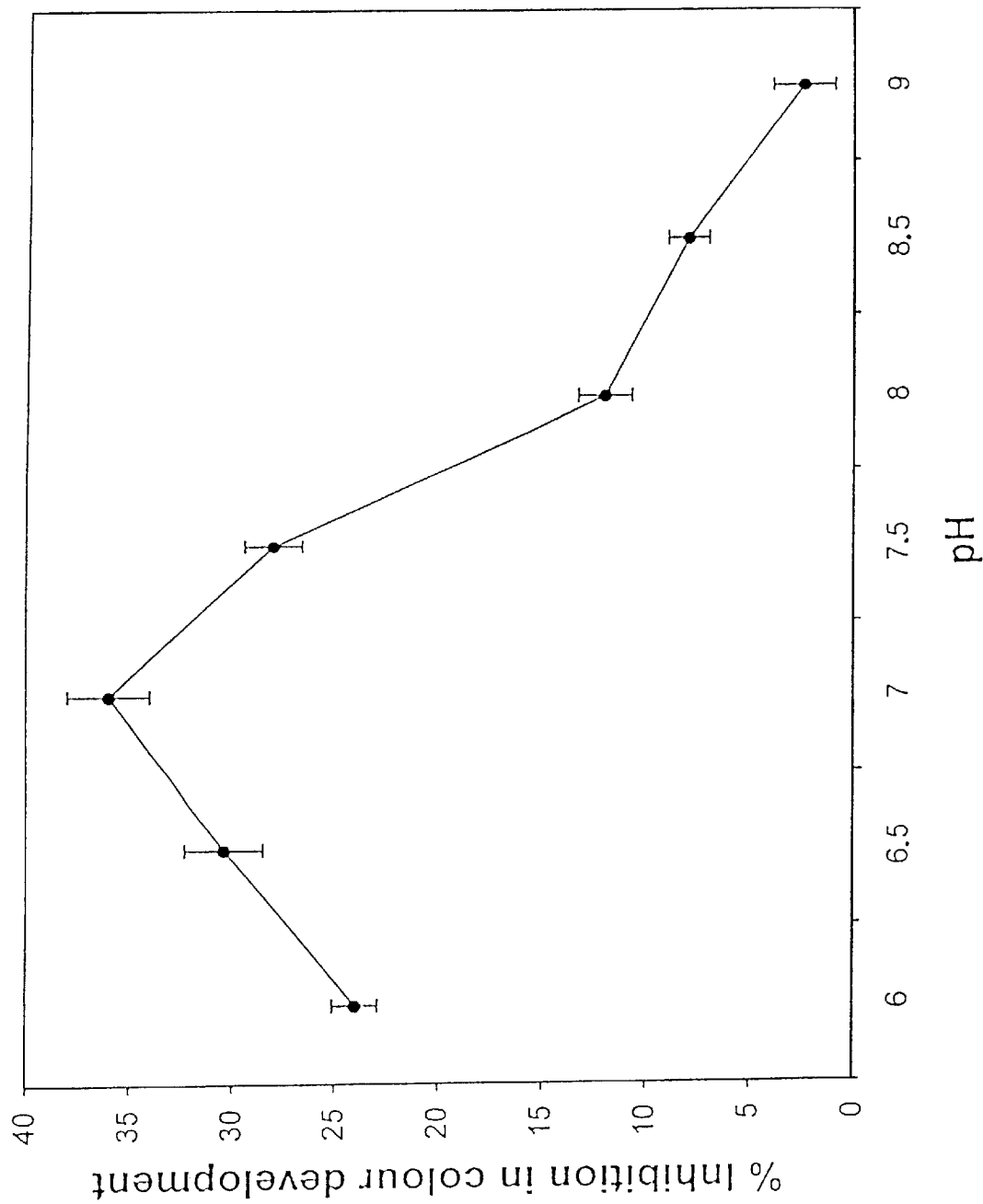
FIG. 1 represents effect of different assay pH on SOD activity in the crude extract at 25° C.

SOD as disclosed in the present invention is extracted from Potentilla, growing at Kunzum Pass (light intensity, 2500μ Einstein/m$^2$/second; day time air temperature, 3–10° C.; altitude 4517 m; 32° 24' 20" N; 077° 38' 40" E) in Lahaul and Spiti district of Himachal Pradesh in Western Himalaya of India. Interestingly, no other plant can be spotted at Kunzum Pass except for Potentilla. Such an environment of low temperature coupled with high light intensity would lead to the generation of $O_2^{-\cdot}$ within the plant cells at a very high rate (Allen, R. 1995. Plant Physiol. 107: 1049–1054) and hence, plant should have enormous capabilities to dismutate $O_2^{-\cdot}$ in order to survive and complete its life cycle. Since Potentilla is the only plant growing abundantly under such harsh environment of Kunzum Pass, this plant was contended as a source of a novel SOD. Potentilla was brought from Kunzum Pass along with the roots and the surrounding soil and established in the plastic pots measuring 15 cm length ×15 cm upper diameter ×7.5 cm bottom diameter at Palampur (32° 04' N, 76° 29' E; altitude, 1300 m). After stabilizing at Palampur for one month to one year, the leaf tissue was used for extraction and purification of SOD. It was necessary to establish the plant Potentilla at Palampur to utilize the laboratory facilities required for extraction and purification of the enzyme. Nonetheless, availability of the facilities at Kunzum Pass will allow the same enzyme to be extracted and purified at sight.

It is implied that the other plants of high altitude and the flora and fauna including micro-flora and micro-fauna growing in the Arctic, Antarctic and Desert would yield novel SOD. Some of the representative plant species from these areas include Helichrysum sp., *Rubus chamaemorus, Polygonum amphidi,* Phillipia sp., *Saxifraga hirculus, Puya raimondii,* Salix sp., *Espeletia schultzii,* Betula sp., *Lupinus alopecuroides,* Alnus sp., Puta sp., *Alchemilla johnstonii* sp., Podocarpus sp., Cyatheas sp., Helichrysum sp., Argyroxiphium sp., *Senecio keniodendron,* Hypericum sp., Arcytophyllum sp., Racomitrium sp., Polytrichum sp., Cetraria sp.

Acacia sp., Prosopis sp., Tamarix sp., Ephedra sp., Capparis sp., Zizyphus sp., Salvadora sp, Calotropis sp., Tribulus sp., Suaeda sp., Ambrosia sp., Yucca sp., Encelia sp., Opuntia sp., Cereus sp., Pachycereus sp., Parthenium sp., Jatropha sp., Agave sp.

In an advantageous embodiment, a method to identify the isozyme of SOD, which shows the activity at temperatures higher that +50° C. and at sub-zero temperatures, has been developed. Development of such a method was intended to targetng the isozyme before the purification could be taken up.

In yet another advantageous embodiment a method to assay the SOD enzyme at sub-zero temperature has been developed wherein inclusion of antifreeze agent glycerol allows monitoring of the enzyme activity at sub-zero temperatures.

In a preferred embodiment, a more complete purification of SOD is accomplished by size fractionation on a size exclusion column of the extract obtained after ion exchange chromatography in order to eliminate the proteins carrying same charge but different molecular weight. Size fractionation has been accomplished using a high pressure liquid chromatography system to save on time.

Yet in another embodiment, SOD has been characterized in terms of its molecular weight, absorption spectrum in ultra-violet (UV) and infra-red range.

Yet in another preferred embodiment, the polyclonal antibody of the SOD has been raised in rabbit and antigenicity was established using relevant tests.

It will be possible to use the product of the invention in the formulations/compositions mentioned below, but not be limited to those mentioned below, which have included SOD as one of the active ingredients:

The present invention will be illustrated in greater details by the following examples. These examples are presented for illustrative purposes only and should not be construed as limiting the invention, which is properly delineated in the claims.

EXAMPLE 1

Preparation of the Crude Extract and Identification of Optimal pH for SOD Activity SOD was assayed at 25° C. at different pH ranging between 6.5 to 9.0 at an interval of 0.5 unit (See FIG. 1) following the inhibition in photoreduction of nitroblue tetrazolium (NBT) by SOD as described by Beauchamp and Fridovich (Anal. Biochem. 1971; 44: 276–287). Leaf tissue was homogenized in homogenizing buffer (10 ml for 1.0 g of fresh weight of leaf tissue) consisting of 0.05 M potassium phosphate buffer, 7% polyvinyl-polypyrrolidone, and 0.025% Triton X-100. Homogenate was centrifuged at 10,000 rpm for 10 min at 4° C. Supernatant (hereinafter, referred to crude enzyme) was decanted and used for SOD assay. Reaction medium contained 0.05 M potassium phosphate buffer (pH ranging between 6.5 to 9.0), $5.7 \times 10^{-5}$ M nitroblue tetrazolium (NBT), $9.9 \times 10^{-3}$ M methionine, $1.17 \times 10^{-6}$ M riboflavin and 0.025% Triton X-100 in a total volume of 3.0 ml. Reaction (performed in a 30 ml glass vial) was initiated by illuminating the reaction with light intensity of $1000 \mu$ Einstein/m$^2$/second using a fibre optic light source (Nikon). The reaction was terminated after 2 min and the absorbance was read at 560 nm.

A control reaction was always performed wherein all the steps and components were exactly the same as described above except that crude enzyme was replaced with equal volume of homogenizing buffer. SOD competes with NBT for $O_2^-$, hence presence of SOD inhibits the color development. Activity of SOD is expressed as per cent inhibition in colour development as compared to the control reaction (higher the inhibition, higher the SOD activity).

As can be seen from the FIG. 1, the enzyme showed pH optima of 7.0. Therefore, all the further experiments were performed at pH of 7.0.

EXAMPLE 2

Effect of Temperature on Crude SOD Activity

Figure 2:
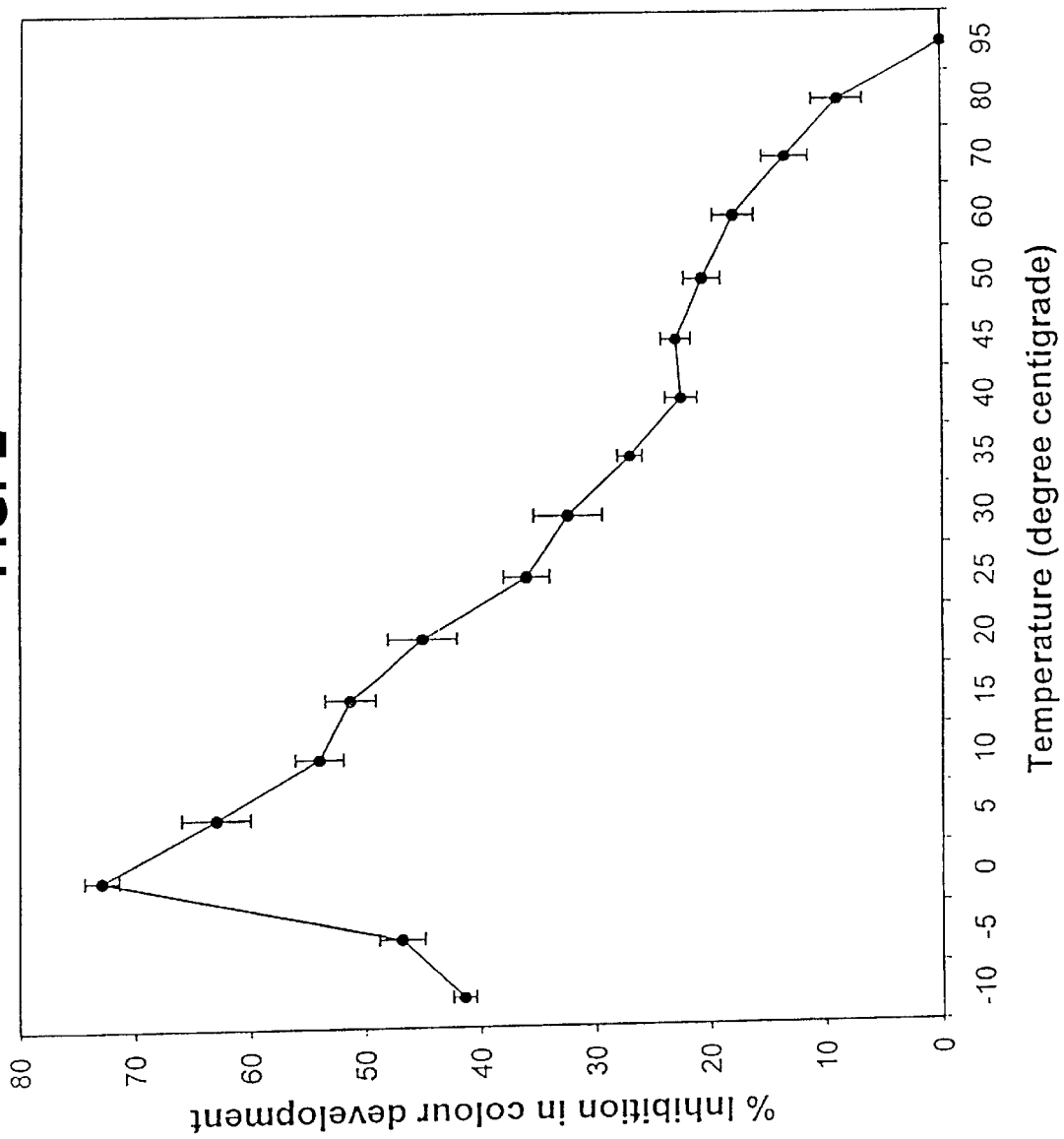
FIG. 2 represents effect of assay temperature on the SOD activity in the crude extract.

The crude enzyme was assayed at temperatures ranging between –10 to 95° C. in the buffer composition as described in Example 1 except that 50% glycerol was added in the reaction mixture to avoid freezing at low temperature. A glass beaker of 100 ml capacity was filled with either alcohol (for working at temperatures of –10, –5, 0° C.) or distilled water (for working at rest of the temperatures) was used to maintain the temperature of the reaction medium while assaying SOD. Reaction medium along with the enzyme was pre-equilibrated at desired temperature to avoid time lag in attaining the required temperature. As can be seen from FIG. 2 that the enzyme showed highest activity (72.9% inhibition) at 0° C. Yet, another novel finding was that the enzyme was functional even upto –10° C. (41.4% inhibition). The applicants feel that the enzyme will be functional even at temperatures below –10° C. When assayed at upto 95° C., the enzyme activity reduced linearly from 0° C. onwards upto 95° C. where the enzyme activity was totally inhibited. Control reactions, as mentioned in Example 1, were always performed at all the temperatures.

EXAMPLE 3

Effect of Boiling and Autoclaving on Crude SOD Activity

To study the thermostability of the enzyme, the crude enzyme was boiled at 100° C. for 60 minutes, cooled down either slowly by leaving at room temperature or by immediate cooling by placing on ice and assayed as mentioned in earlier Example 2 at –10 to 95° C.

A comparison of the enzyme activity before and after the boiling showed that the activity of the enzyme was sustained without any loss (See Table 1).

A rigorous test on thermostability was performed by autoclaving the crude enzyme and then performing assay at –10 to 80° C. As is evident from Table 1 that the activity of the enzyme was sustained with 12 to 35% loss at different temperatures.

TABLE 1

Effect of boiling and autoclaving the crude extract on the SOD activity at different temperatures

| Treatment Temperature (° C.) | Enzyme activity (% inhibition in color development) | | |
|---|---|---|---|
| | Before Boiling | After Boiling | After Autoclaving |
| –10 | 24.3 ± 0.45 | 24.5 ± 0.18 | 16.8 ± 1.90 |
| –5 | 30.0 ± 0.11 | 29.8 ± 0.27 | 24.4 ± 1.20 |
| 0 | 76.1 ± 0.94 | 76.5 ± 0.73 | 66.5 ± 1.70 |
| 5 | 69.4 ± 0.34 | 69.2 ± 0.12 | 60.1 ± 0.99 |

TABLE 1-continued

Effect of boiling and autoclaving the crude extract on the
SOD activity at different temperatures

| Treatment | Enzyme activity (% inhibition in color development) | | |
|---|---|---|---|
| Temperature (° C.) | Before Boiling | After Boiling | After Autoclaving |
| 25 | 37.0 ± 0.03 | 37.9 ± 0.59 | 27.7 ± 0.41 |
| 40 | 23.1 ± 0.19 | 23.0 ± 0.13 | 16.3 ± 1.60 |
| 80 | 8.2 ± 0.65 | 8.1 ± 0.15 | 5.4 ± 0.29 |

EXAMPLE 4

Method of Identification of the Target Isozyme of the SOD for the Purpose of Purification The above Examples 2 and 3 are suggestive of novel SOD not described hitherto. Hence, it was essential to know if all the isozymes or any one of them depicts the above mentioned properties. A method was, therefore, developed to monitor the activity of various isozymes between sub-zero to +60° C. The isozymes showing good activity at these temperatures was targeted for the purpose of purification and tested for autoclavability. Since crude extract shows the SOD activity after autoclaving, it was contemplated that any isozyme showing prominent activity at this temperature amplitude should show the property of autoclavability as well.

Figure 3:
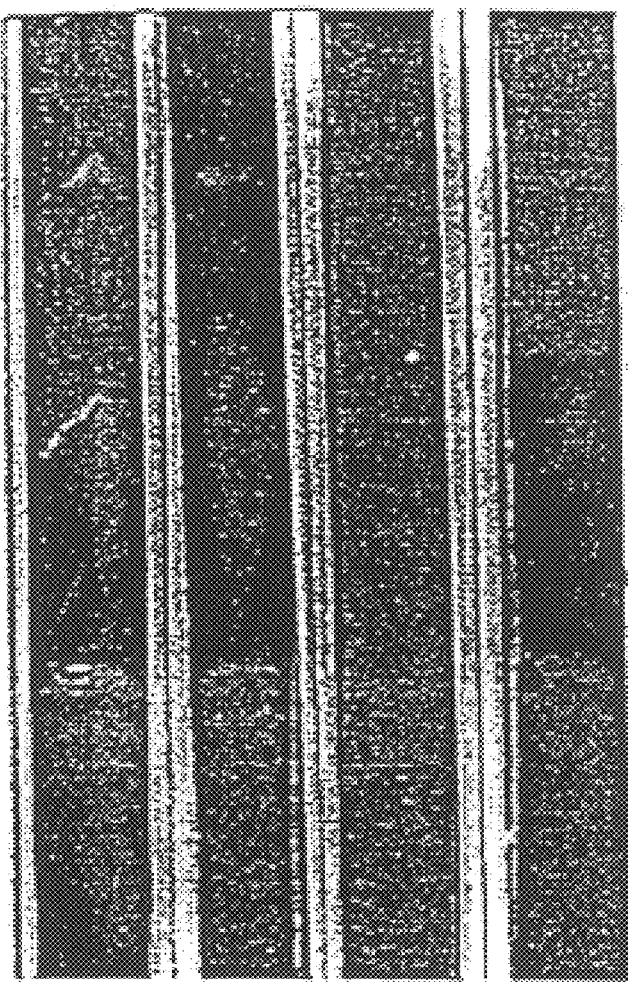
FIG. 3 represents identification of isozyme of SOD to be targeted for the purification.

To achieve this:
(a) various isozymes of SOD in the crude extract of the leaf were localized on 10% native polyacrylamide gel as described by Beauchamp and Fridovich (Anal. Biochem. 1971. 44,276–287).
(b) After electrophoresis, gel was rinsed with distilled water followed by 30 minute incubation in 2.5 mM NBT. Gel was then immersed in $1.17 \times 10^{-6}$ M riboflavin for 20 minute and removed later onto a petri plate to expose to a light intensity of 1000 $\mu$ Einstein/m$^2$/second using a fiber optic light source (Nikon). Light exposure led to photogeneration of $O_2^-$, which converts NBT into insoluble purple colored formazan. As a result, purple color is developed throughout the gel except for the locations where SOD was localized.
(c) Incubation with NBT and riboflavin, and light exposure was carried out at 4 different temperatures of –20, 4, 25 and 60° C.
(d) When working at –20° C., glycerol (50% final concentration) was added in the incubation solution to avoid freezing.
(e) As can be seen from FIG. 3 that out of 4 isozymes with Rf values (distance of protein migration/distance of tracking dye migration) of 0.33, 0.55, 0.565, 0.589, the intensity of only one isozyme with Rf value of 0.55 was most prominent at all the temperatures.
(f) Staining intensity of rest of the isozymes was comparatively lower. Therefore, the isozyme with Rf of 0.55 was identified as a most stable isozyme and considered to be novel. This isozyme was targeted for the purpose of purification.

EXAMPLE 5

Process for Purification of SOD

The targeted novel isozyme of SOD was purified as follows not described hitherto. Hence, it was essential to purify the enzyme and then study the properties.

Figure 4:
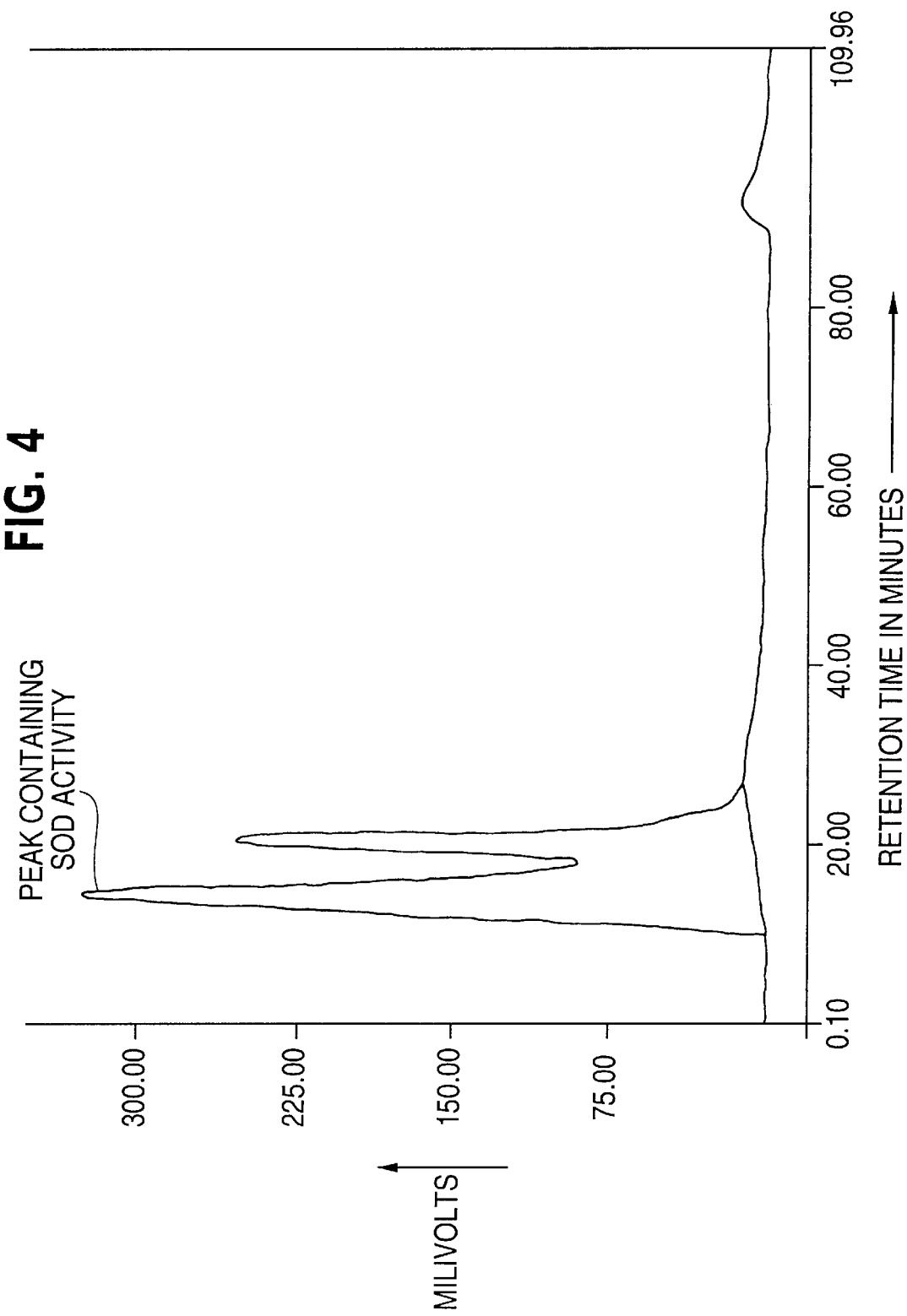
FIG. 4 represents fractionation of the SOD on a TSK gel column (G 2000 SW).
Figure 5:
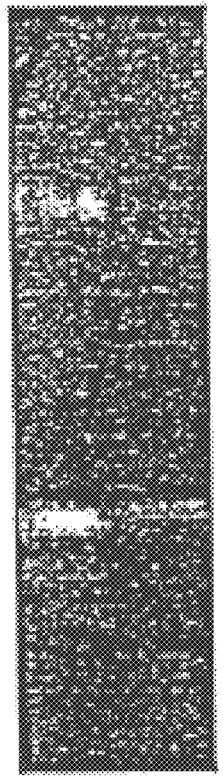
FIG. 5 represents localization of the isozymes of SOD in the crude extract (C) and purified isozyme of SOD (P) on a polyacrylamide gel.

(a) homogenizing leaf tissue (100 g) in 1 L of homogenizing buffer (0.05 M potassium phosphate buffer, pH 7.0 (autoclaved); 7% PVPP; 1 mM PMSF) at 4° C.;
(b) filtering the homogenate through 4 layers of muslin cloth and centrifuging the filtrate at 10, 000 rpm for 20 minutes at 4° C.;
(c) decanting the supernatant for purification of SOD;
(d) precipitating SOD with 30–60% ammonium sulfate (30–60% fraction);
(e) dissolving precipitate in phosphate buffer (0.05 M potassium phosphate buffer, pH 7.0; autoclaved) and dialyzing for.24 hours with 8 changes of phosphate buffer;
(f) loading the dialyzed protein onto a DEAE-Cellulose column and eluting with 50 mM of 250 ml of potassium chloride (KCl) solution followed by 250 ml of 200 mM KCl solution and finally eluting with 250 ml of 500 mM of KCl Solution (solution of KCl was prepared in 10 mM phosphate buffer; all autoclaved).
(g) assaying fractions containing protein for SOD.
(h) Fractionating SOD containing fractions were using a size exclusion column (TSK, G 2000 SW) on a high pressure liquid chromatography (Data system 450, Kontron Instruments, Switzerland) using 200 mM KCl prepared in 10 mM phosphate buffer (all autoclaved) with a flow rate of 1.0 ml per minute. This step eliminated other proteins carrying same charge but different molecular weight
(i) Assaying each peak obtained after HPLC (See FIG. 4) for SOD assay and concentrating using Centricon protein concentrator column from Amicon (Centricon-10; 10, 000 MW cut-off).
(j) Assaying Concentrated protein for SOD activity at different temperatures ranging between –10 to +80° C. Glycerol (50% final concentration) was added in the reaction buffer to avoid freezing at sub-zero temperatures.
(k) Localizing Purified SOD on 10% SDS polyacrylamide gel as described by Beauchamp and Fridovich (Anal. Biochem. 1971; 44: 276–287). After electrophoresis, gel was rinsed with distilled water followed by 30 minute incubation in 2.5 mM NBT. Gel was then immersed in $1.17 \times 10^{-6}$ M riboflavin for 20 minute and removed later onto a petri plate to expose to a light intensity of 1000 $\mu$ Einstein/m$^2$/second using a fibre optic light source (Nikon). Light exposure led to photogeneration of $O_2^-$, which converts NBT into insoluble purple colored formazan. As a result, purple color is developed throughout the gel except for the locations where SOD was localised. As can be seen from FIG. 5 only single band of SOD isozyme was observed when purified fraction was loaded compared to several isozymes in the crude extract.

EXAMPLE 6

Confirmation of the Purified Isozyme of the SOD as a Single Protein

Figure 6:
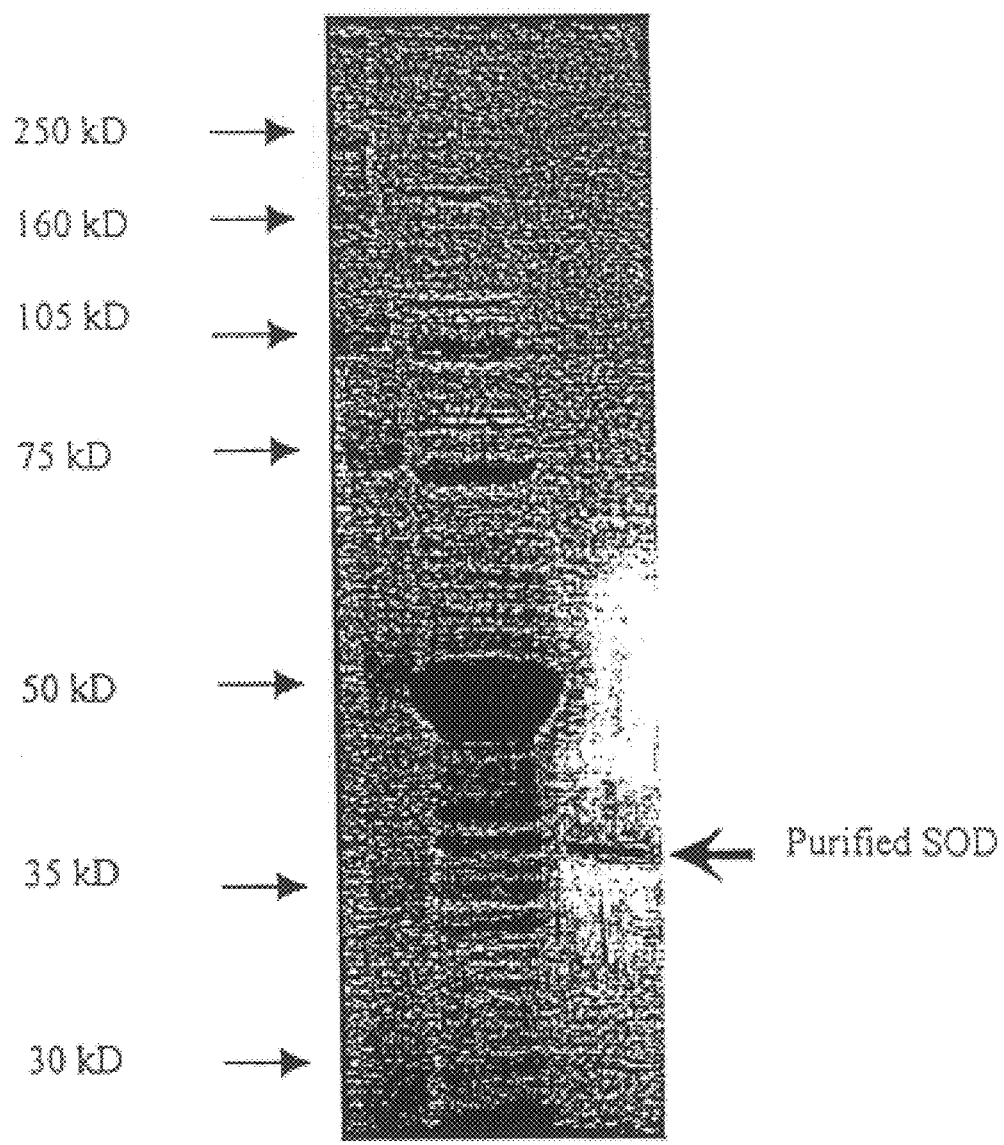
FIG. 6 represents localization of soluble proteins in the crude extract (C) and purified isozyme of SOD (P) on a polyacrylamide gel by staining through Coomasie Brilliant Blue dye R-250.

To confirm the purified isozyme of the SOD as a single protein, it was localized on a 10% SDS polyacrylamide gel as described by Laemmeli, U. K. (1970; Nature, 227: 680–685). Rainbow molecular weight markers (catalogue number, RPN800) purchased from Amersham Pharmacia Biotech, USA, suitable for SDS polyacrylamide gels were also loaded in an adjacent well. Thus after completing the electrophoresis, the gel was soaked in a fixative solution (400 ml of methanol, 70 ml of acetic acid and 530 ml of water; all mixed together) for 2 hours and then soaked in a staining solution (0.5 g Coomassie Brilliant Blue R dissolved in 500 ml of fixative solution) for 18 hours. The gel was destained by dipping in fixative solution for 20 hours. Four to five changes of the fixative solution were required for proper de-staining of the gel. Gel was then transferred into 7% acetic acid solution for storage. As can be seen from FIG. 6 that a single protein band was obtained after purification compared to several bands in the crude extract, thus confirming a highly purified single protein.

EXAMPLE 7

Estimation of Molecular Weight of the Purified Isozyme of SOD

Molecular weight of the purified isozyme of SOD was determined on a native polyacrylamide gel and on a sodium dodecyl sulphate (SDS) gel using molecular weight markers from Sigma Chemical Company, St. Louis, USA essentially as detailed in their instruction manual. The molecular weight of the native protein was found to be 33 kilo Dalton (kD), whereas under denatured condition of SDS, the molecular weight was 36 kD. Slightly lower molecular weight of the native protein compared to the denatured protein could be because of difference in the shape, degree of hydration and partial specific volume of the protein standards compared to the protein in question (Hames, B. 1990. In Hames, B. D. and Rickwood, D. Gel electrophoresis of Proteins: A practical Approach, $2^{nd}$ Edition, 383 p., IRL Press at Oxford University Press, Oxford, ISBN 0-19-963075-5). Similar molecular weight under the native and denatured conditions shows that the protein is monomer of approximately 36 kD.

EXAMPLE 8

Absorption Spectrum of SOD

Figure 7:
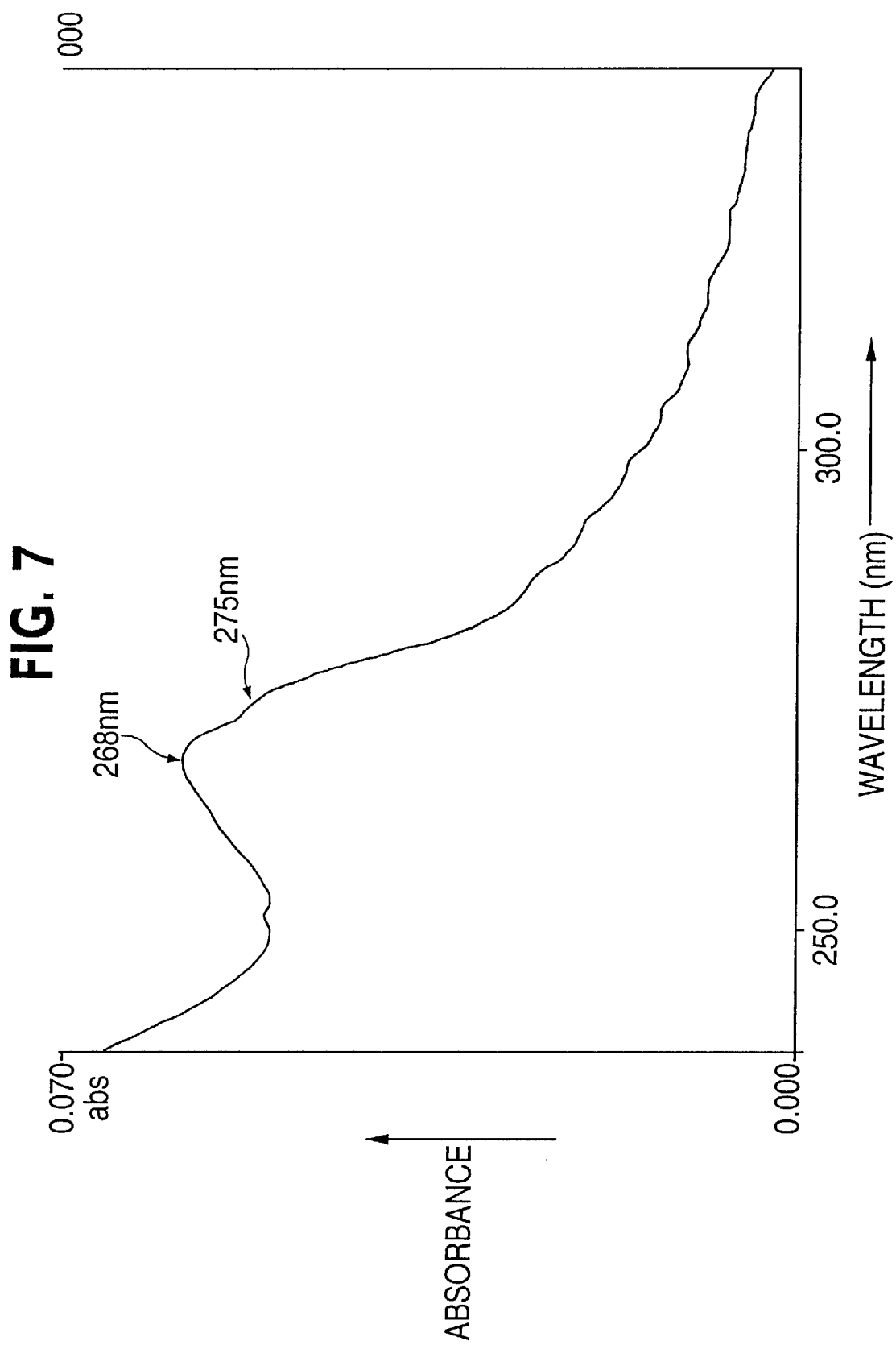
FIG. 7 represents the ultra-violet absorption spectrum of the purified SOD in 50 mM phosphate buffer (pH, 7.0) at 25° C.

Absorption spectrum was recorded using Hitachi 150–20 UV/Visible spectrophotometer from model. Purified SOD exhibited strong absorption in UV range (190–340 nm). A UV absorption spectrum of the purified SOD exhibited peak at 268 nm which shows the presence of phenyl alanine amino acid (hydrophobic in nature) in the protein. Further shoulder at 275 nm shows the presence of tyrosine (a polar amino acid) (See FIG. 7). Absorption spectrum of the enzyme in visible range (340–900 nm) did not show any peak or shoulder.

EXAMPLE 9

Fourier Transformed Infra-Red (FTIR) spectrum of SOD

Figure 8:
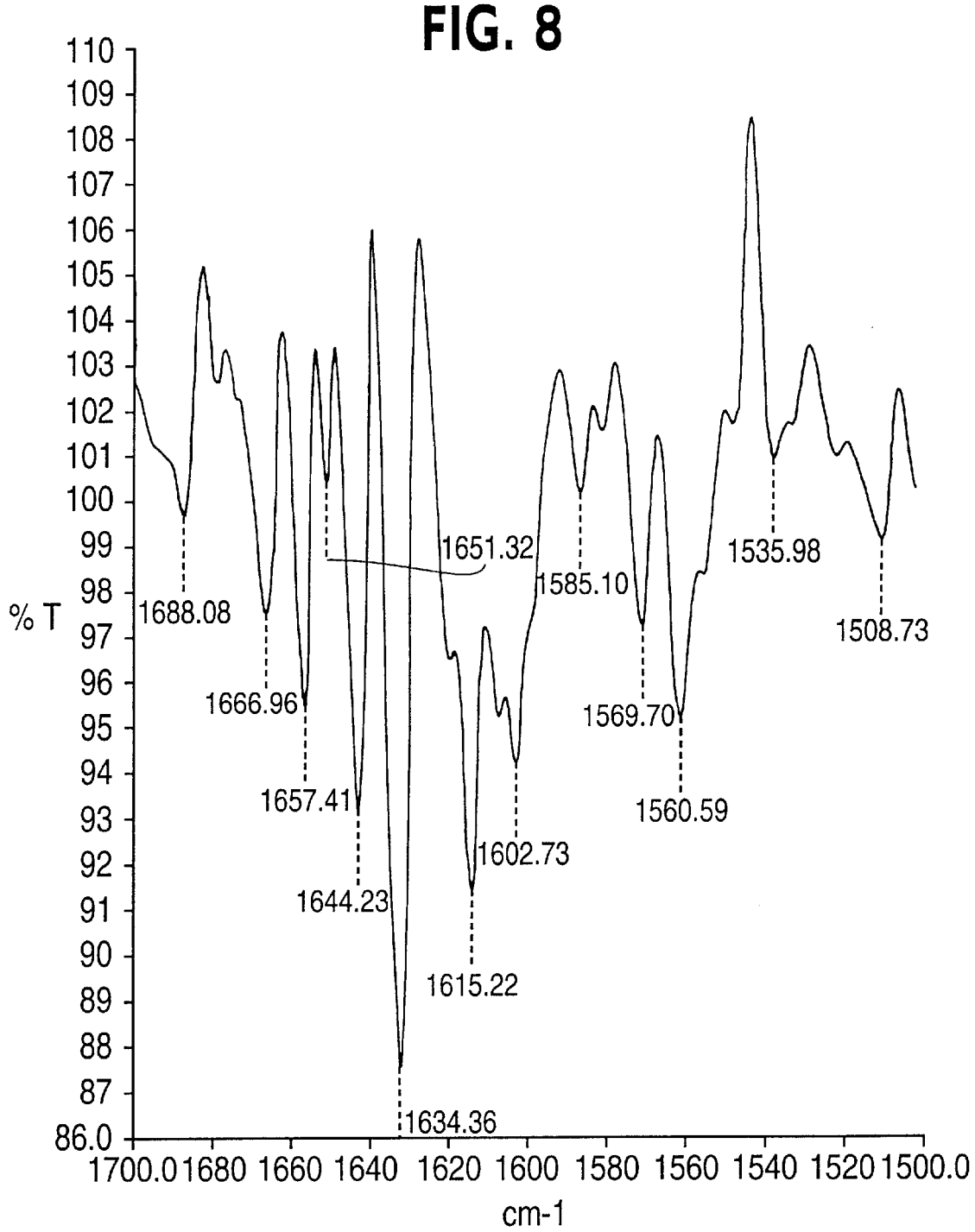
FIG. 8 represents the FTIR spectrum of the purified SOD in 50 mM phosphate buffer (pH, 7.0) at 25° C.

FTIR spectrum of the the SOD was recorded in 50 mM potassium phosphate buffer, pH 7.0, to fingerprint the purified protein (Perkins, W. D. 1987, J. Cem. Edu. 64: A296–A305; Haris, P. I. And Chapman, D. 1988, Chemistry in Britain, October 1988: 1015–1018) using FTIR Spectroscope from Perkin-Elmer model 1760 using far recovery deutoriated tri-glycine sulphate (FR-DTGS) detector at an optical path difference velocity of 0.2 cm $s^{-1}$. As can be seen from FIG. 8 that purified SOD exhibited absorption at 1657.41 $cm^{-1}$ and 1666.96 $cm^{-1}$, which is indicative of α-hellicle structure of the isozyme. Other major peak of the isozyme was recorded at 1644.23, 1634.36 and 1615.22 $cm^{-1}$.

EXAMPLE 10

Effect of Temperature on Purified SOD

Purified SOD was assayed (6 ng was used for each assay) at different temperatures ranging between −10 to 95° C. as described in Example 2. As can be seen in Table 2, the highest activity was recorded at 0° C. (70.7% inhibition) with linear decrease in activity upto 80° C. (8.8% inhibition). As with the crude extract, the enzyme showed activity even at −10° C. (26.6% inhibition).

When purified SOD was autoclaved (121° C., at 1.1 kg per square cm for 20 minutes) and then assayed at different temperatures, the activity remained the same as before the autoclaving. Meaning thereby, that the SOD was tolerant to autoclaving. Interesting point was that the SOD in the crude extract showed some loss in the activity, but the purified SOD did not show any loss in the activity.

A calculation of an enzyme turnover number (or also known as catalytic constant) before and after autoclaving yielded a value of $19.53\times10^4$ and $19.44\times10^4$% inhibition per nmole of enzyme per min, respectively. Meaning thereby, that the autoclaving had no effect on the turnover number of the enzyme. Turnover number was calculated as follows:

$$k_2 = V_m / [E_t]$$

Figure 9:
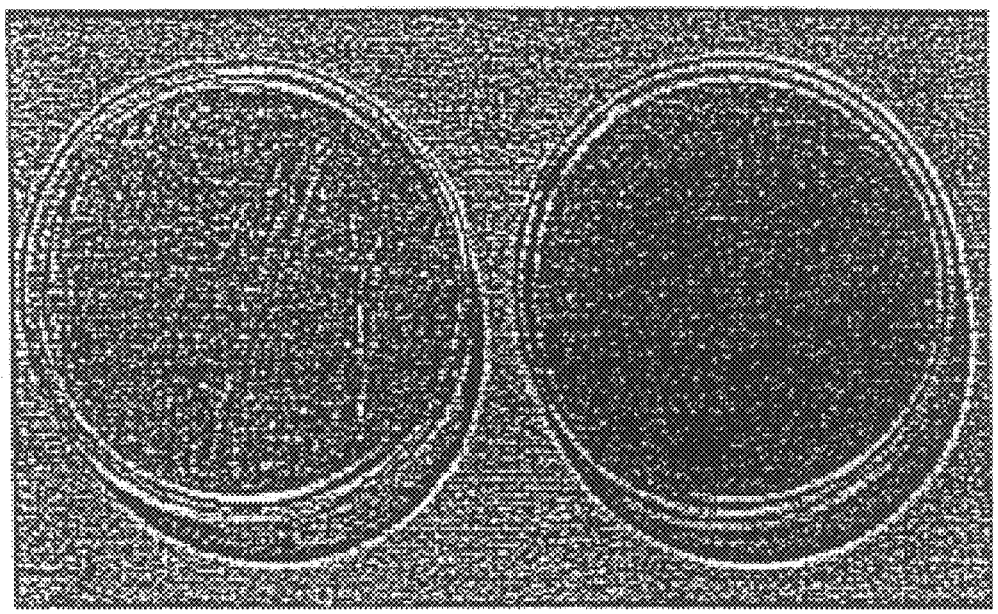
FIG. 9 represents absence of microbial contamination in the purified SOD after autoclaving.

Where:

$k_2$ is turnover number; $V_m$ is maximum velocity; $[E_t]$ is calculated as 6 ng per 3 ml. divided by 33,000 (molecular weight under non-denaturating conditions) ng per nmol. Also streaking of the autoclaved and purified SOD on Luria-Bertani (LB) medium plate did not show any microbial growth (FIG. 9).

TABLE 2

Effect of autoclaving the purified SOD on its activity at different temperatures

| Treatment | Enzyme activity (% inhibition in color development) | |
| --- | --- | --- |
| Temperature (° C.) | Before autoclaving | After autoclaving |
| −10 | 26.6 ± 1.11 | 25.3 ± 0.70 |
| −5 | 36.2 ± 1.92 | 35.5 ± 1.76 |
| 0 | 70.7 ± 0.68 | 70.4 ± 1.15 |
| 5 | 56.1 ± 2.01 | 56.0 ± 1.71 |
| 25 | 20.1 ± 0.39 | 20.4 ± 0.19 |
| 40 | 21.1 ± 0.31 | 20.2 ± 0.29 |
| 80 | 8.7 ± 0.4 | 8.8 ± 0.3 |
| 95 | 0 | 0 |

EXAMPLE 11

Effect of Inhibitors on SOD Activity

Purified SOD was completely inhibited either by potassium cyanide (1 mM) or hydrogen peroxide (1 mM) (See Table 3). It is known that depending upon the co-factor requirements, the SOD can be Mn-SOD (SOD requiring manganese as a co-factor, insensitive to potassium cyanide and hydrogen peroxide), Cu/Zn-SOD (SOD requiring copper and zinc as co-factors; sensitive to potassium cyanide and hydrogen peroxide) and Fe-SOD (SOD requiring iron as a co-factor; sensitive to hydrogen peroxide but insensitive to potassium cyanide) (Bowler, C, Montagu, M. V. and Inze, D. 1992. Annual Review of Plant Physiol. and Mol. Biol. 43: 83–116). The SOD reported in the present invention is inhibited by both KCl and H$_2$O$_2$, and hence represents Cu/Zn SOD.

TABLE 3

Effect of inhibitors on the activity of purified SOD assayed at 25° C.

| Treatment | SOD Activity (% inhibition in color development) |
|---|---|
| Control | 20.39 ± 0.27 |
| +1 mM Potassium cyanide | 0 |
| +1 mM Hydrogen peroxide | 0 |
| +1 mM Potassium cyanide + 1 mM hydrogen peroxide | 0 |

EXAMPLE 12

Raising Antibodies Against SOD in Rabbit and Testing of Antigenicity Using Ouchterlony's Double Diffusion Test Polyclonal antibodies against SOD were raised in rabbit by injecting SOD purified (100 ng in 500 μl of potassium phosphate buffer; pH, 7.0) mixed with complete Freund's adjuvant followed by three booster dosage of SOD mixed with incomplete Freund's adjuvant at weekly intervals. Complete Freund's adjuvant was obtained from Bangalore Genei, India that contained paraffin oil, mannide monooleate as an emulsifier and heat-killed *Mycobacterium tuberculosis*. Any other adjuvant system such as the Ribi Adjuvant system, muramyl peptides, wax fractions of purified cell walls of Mycobacterium, N-acetylmuramyl-L-alanyl-D-isoglutamine, dimethyldioctadecyl ammonium bromide, a lipoidal quaternary ammonium compound, Amycolate or any other available commerically or otherwise may be used to elicit the immune response.

Adjuvant (500 μl) was thoroughly emulsified with the purified enzyme ((500 μl; 100 μg) to obtain a stable antigen-antibody emulsion by rapidly withdrawing and expelling the antigen-adjuvant mix using a 22 gauge needle fitted to a sterile syringe. Complete emulsification was tested by placing a drop of the mixture onto a still surface of distilled water. The intactness of the droplet assures complete mixing. Antigen-adjuvant mixture (800 μl) was injected in thigh muscles of a rabbit weighing 3 kilogram using a 22 gauge needle.

Blood was collected from heart of the rabbit and allowed to clot for 2 hours at room temperature. After overnight storage at 4° C., the edges of the clot were rimmed using a Pasteur pipette and centrifuged at 150 g for 5 min. Supernatant was collected and centrifuged for 15 min at 350 g to remove cell debris. Sodium azide was added to a concentration of 0.025% and the serum was stored at 4° C.

Ouchterlony's double diffusion test was performed as described by Kanematsu, S. and Asada, K. (Plant Cell Physiol. 31: 99–112; 1990). Thus, in a 85 mm petri plate, 1.5% agar prepared in 0.15 M NaCl, 20 Mm potassium phosphate of pH 7.0 and 0.02% sodium azide was poured to a thickness of 3 mm. Antigen (20 μl containing 4 μg of protein) and antibody were loaded into the 3 mm diameter well cut with the help of a cork-borer. Petri plate was covered and kept in a humid environment for 16–24 hours at 37° C. and examined for a line of immune precipitation.

Figure 10:
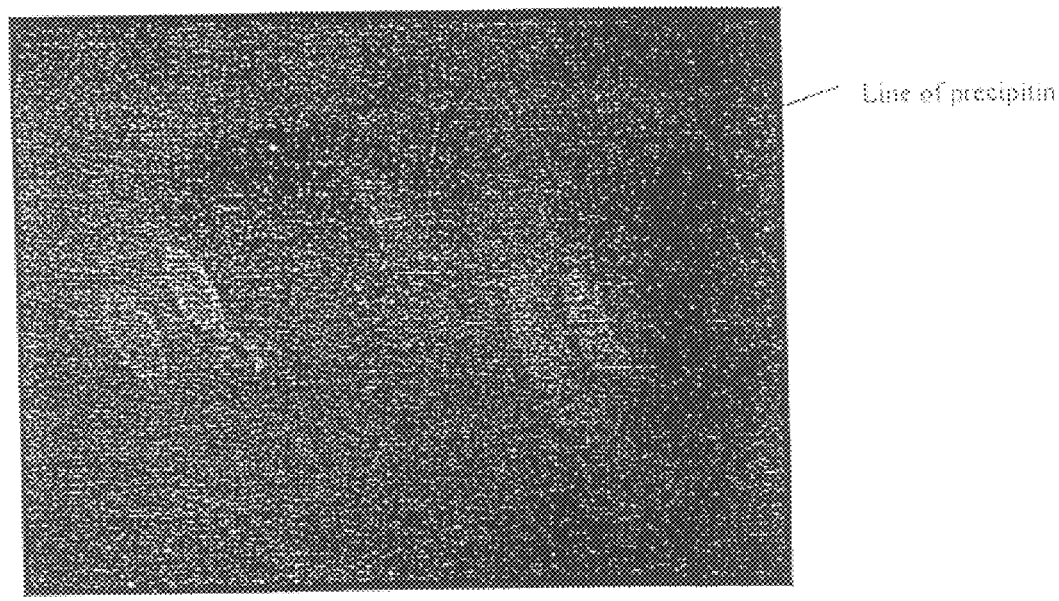
FIG. 10 represents testing of antigenicity of the antibody raised in rabbit against the purified isozyme of the SOD by Ouchterlony double diffusion test.

As can be seen in FIG. 10 a line of immune precipitation confirms the antibody production against the purified enzyme.

EXAMPLE 13

Figure 11:
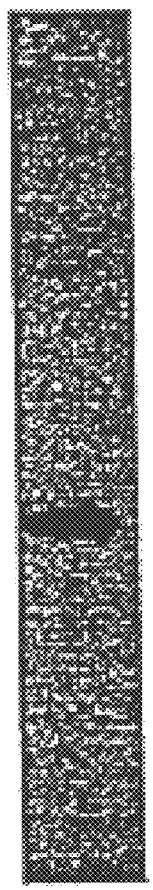
FIG. 11 represents testing of antigenicity of the antibody raised in rabbit against the purified isozyme of the SOD by Western Blotting.

Testing of Antigenicity of the Antibodies Raised in Example 12 Using Western Blotting Ouchterlony's double diffusion test showed antigencity of the antibody against the purified isozyme of the SOD. This was further confirmed using western blot analysis as described by Sambrook, J., Fritsch, E. F., Maniatis, T. (1989; Molecular Cloning, a laboratory Manual, 2$^{nd}$ edition, Cold Spring Harbor Laboratory Press, New York, USA). Purified isozyme of the SOD was run on a 10% sodium dodecyl sulphate (SDS) gel as described by Laemmeli, U. K. (1970; Nature, 227: 680–685). Protein was transferred onto a polyvinylidene fluoride (PVDF) membrane, Immobilon™-P$^{SQ}$ purchased from Millipore, U.S.A., using wet blotting apparatus from Consort, Belgium. Blotting was carried out using a transfer buffer of pH 8.3 consisted of 25 mM Tris, 100 mM glycine and 20% methanol at a 70 Ma for 12 hours. A light emitting non-radioactive reagent for detection of immobilized purified protein was purchased from Amersham-Pharmacia Biotech, U.S.A. and manufacturer's instructions were followed to detect the antigen-antibody reaction. FIG. 11 shows a strong single band, which further confirms the antibody raised against the purified isozyme of the SOD.

EXAMPLE 14

Effect of Storage Conditions on SOD Activity

Purified SOD was tested for its longevity at 4 and 25° C. SOD did not exhibit any loss of activity even after 6 months of storage at 4° C. At 25° C., the enzyme activity reduced by 20.6% in 5 days with no further decrease till 25 days. When measured on day 30, the activity reduced by 33% of the original activity (See Table 4).

Figure 12:
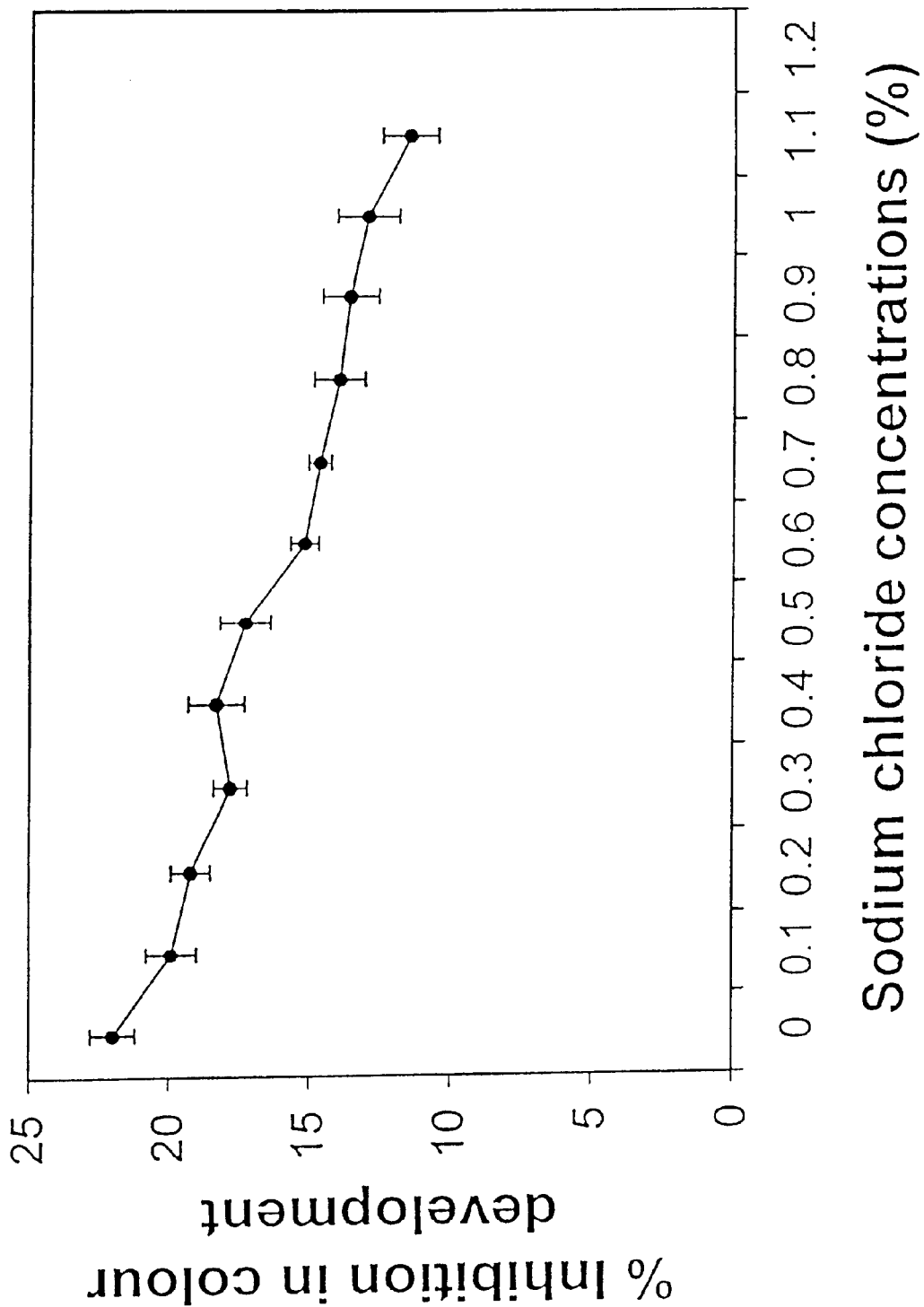
FIG. 12 represents effect of different sodium chloride concentrations on the activity of purified SOD at 25° C.

Purified SOD was also tested for its activity in the presence of sodium chloride. The SOD activity decreased by 50% as the concentration of sodium chloride increased from 0 to 1.2%. At 0.9% of sodium chloride concentration (concentration used in saline injection) the purified SOD was active, however, the activity reduced by 38.9% of the zero per cent sodium chloride concentration (See FIG. 12).

TABLE 4

Effect of storage temperature on the activity of purified SOD (% inhibition in color development) assayed at 25° C.

| Day | Storage temperature | |
|---|---|---|
| | 4° C. | 25° C. |
| 0 | 21.1 ± 0.50 | 21.8 ± 0.50 |
| 5 | 20.5 ± 1.23 | 17.3 ± 0.49 |
| 10 | 21.0 ± 1.50 | 17.2 ± 0.88 |
| 15 | 20.0 ± 0.88 | 17.49 ± 1.70 |
| 20 | 20.1 ± 1.26 | 17.9 ± 0.87 |
| 25 | 21.1 ± 1.05 | 17.5 ± 0.72 |
| 30 | 20.9 ± 1.05 | 14.6 ± 0.10 |

EXAMPLE 15

SOD Activity at Different Temperatures in Pea and Barley Leaf Tissue

Crude enzyme from the leaf tissue of pea and barley grown at Palampur was extracted and assayed essentially as described in Examples 1, 2 and 3 at different temperatures. As can be seen from Table 5 that the enzyme did not show any activity below 5° C. and the activity of the enzyme was lost upon boiling or autoclaving.

TABLE 5

Effect of temperature on the activity of SOD (% inhibition in color development) in Barley and Pea

| Treatment Temperature (° C.) | Enzyme activity (% inhibition in color development) | |
|---|---|---|
| | Barly | Pea |
| 0 | 0 | 0 |
| 5 | 3.11 ± 1.19 | 2.91 ± 0.98 |
| 10 | 60.47 ± 1.13 | 65.58 ± 1.93 |
| 15 | 54.13 ± 0.97 | 56.98 ± 1.05 |
| 20 | 40.26 ± 1.01 | 44.15 ± 1.7 |
| 25 | 29.49 ± 2.1 | 32.24 ± 1.99 |
| 30 | 23.59 ± 2.2 | 25.44 ± 1.75 |
| 80 | 0 | 0 |

EXAMPLE 16

SOD Activity at Different Temperatures in *Geum elatum* an Another Plant Species Growing at High Altitude of 4000 m As can be seen in Table 6, the activity of the SOD enzyme in the crude extract from the leaf tissue of *Geum elatum*, extract prepared as mentioned in Example 1, and assayed as mentioned in example 2 and 3, showed that:

(a) The activity remains unaffected after boiling or after autoclaving (b) The enzyme shows highest activity at zero degree centigrade The enzyme remains active at sub-zero temperature of −10° C.

TABLE 6

Effect of boiling and autoclaving the crude extract of *Geum elatum* on the SOD activity assayed at different temperatures

| Treatment Temperature (° C.) | Enzyme activity (% inhibition in color development) | |
|---|---|---|
| | Before Boiling | After Boiling |
| −10 | 46.46 ± 0.99 | 45.65 ± 0.76 |
| −5 | 51.53 ± 0.61 | 52.06 ± 1.06 |
| 0 | 76.33 ± 1.11 | 74.46 ± 1.97 |
| 5 | 64.93 ± 0.50 | 65.13 ± 0.55 |
| 25 | 42.67 ± 0.58 | 43.34 ± 1.34 |
| 40 | 24.66 ± 0.65 | 24.83 ± 0.71 |
| 80 | 3.40 ± 0.41 | 3.05 ± 0.21 |
| After Autoclaving and assaying at 25° C. | | 41.33 ± 1.22 |

EXAMPLE 17

Effect of Long Term Storage of SOD Activity

As can be seen from the Table 7, that the storage of SOD at 4° C. even upto 12 months does not affect the activity of the enzyme.

TABLE 7

Effect of storage period on the activity of purified SOD (% inhibition in color development) assayed at 25° C.

| Storage period (Months) | Enzyme activity |
|---|---|
| 0 | 22.25 ± 1.17 |
| 2 | 21.05 ± 0.95 |
| 4 | 22.07 ± 1.01 |
| 6 | 20.98 ± 1.55 |
| 8 | 22.19 ± 1.06 |
| 10 | 21.1 ± 1.12 |
| 12 | 22.0 ± 1.05 |

The main advantages of the present invention are:

1. For the first time, a SOD enzyme has been identified which can be autoclaved. The isozyme can be autoclaved to give a germ free sterile preparation. It functions at temperature ranging from sub-zero to,80° C.
2. The identified SOD functions efficiently at low temperature of 0° C. the enzyme showed substantial activity at −10° C. (41.4% inhibition) and the enzyme is expected to function at temperatures lower than −10° C.
3. The feature of autoclavability and functioning at low temperature, is shown by the same SOD.
4. It has been shown for the first time that SOD can function even at sub-zero temperatures.
5. The autoclaved preparation of the SOD is free from microbial contamination, hence, will be of immense use in medical, cosmetic and food industry.
6. A SOD which remains stable at ambient temperature (25° C.) for one month without adding any stabilizing agent.
7. A process to assay SOD activity upto −10° C.
8. A method to identify the isozyme showing the desired properties before the purification is taken up.
9. A process to purify an autoclavable SOD enzyme which can function between +80 to −10° C.
10. A process for more complete purification of SOD to eliminate the proteins carrying same charge but different molecular weight.
11. The composition prepared according to the invention is a sterile, germ free preparation. The specific activity of SOD described in the prior art was 8037 Units per mg of protein (U.S. Pat. No. 5925363) or 2000 Units per mg of protein (U.S. Pat. No. 5137820). The specific activity obtained in our patent is 66,000 Units per mg of protein, which is substantially higher than those reported so far. This implies that to obtain the same activity, we need to use much lower quantity of protein, while using the novel SOD as claimed in claim 1 of our patent. Other patents used the following quantity of SOD:

| Patent number | Quantity of SOD used |
|---|---|
| 5904921 | 5% |
| 5470876 | 0.1–0.25% |
| 5470876 | 1 g per 100 ml |

Particularly, for the applications intending removal of $O_2^{-\cdot}$ at low temperature of 0–5° C. (claim number 118), the SOD as claimed in claim 1 will have the advantage of higher activity as compared to the other reported SOD, because of lower temperature optima (0° C.) of the SOD reported in our patent.

Comparison of SOD activity data:

SOD activity at 25° C.

| Plant Species | Crude extract | Purified | Reference |
|---|---|---|---|
| Pea | 5.4 U per mg protein | | Our data (Example 15) |
| Barley | 5.9 U per mg protein | | Our data (Example 15) |
| Nicotiana asteroides | 22.6 U per mg protein | 1336 U/mg protein | Beaman, B.L.; Scates, S.M.; Moring, S.E.; Deem, R.; And Misra, H.P.; Journal of Biological Chemistry, 258: 91–96, 1983; Steinman, H.M.; Journal of Biological Chemistry, 257, 10283–10293 |
| Spinach | 6 U per mg protein | 8427 U per mg protein | Kanematsu, S. and Asada, K. 1990, Plant Cell Physiol., 31: 99–112. |
| Alfalfa | 13 U per mg protein | | Mckersie, B.D., Chen, Y., de Beus, M., Bowley, S.R., Bowler, C., Inze, D., D'Halluin, K., Botterman, J. 1993. Plant Physiol. 103: 1155–1163 |
| Vigna radiata | 11.3 U per mg protein | | Reddy, C.D. and Venkaiah, B. 1984. J. Plant Physiol.116: 279–284. |
| Picea abies | 113 U mg protein | 40,000 U per mg protein | Kroniger, W., Rennenberg, H., and Polle, A. 1992. Plant Physiol., 100: 334–340. |
| Potentilla | 8.2 U per mg protein | 66,000 U per mg protein | Our data (Example 10) |

Criticality of purified isozyme of SOD in formulation:
1. The isozyme could be autoclaved to give a germ free sterile preparation
2. The isozyme functions at temperature ranging sub-zero to 80° C.

What is claimed is:

1. A purified isozyme of a superoxide dismutase (SOD) extracted from the plant *Potentilla atrosanguinea Lodd.* Var. *orgyrophylla,* said isozyme having the following characteristics:

(a) $O_2^-$ scavenging activity remains same before and after autoclaving;

(b) scavenges $O_2^-$ from sub-zero temperature of −20° C. to high temperature of+80° C.; and (c) contamination free and infection free from any living micro- and/or macro-organism after autoclaving.

2. A purified isozyme of SOD as claimed in claim 1 which is stable at 4° C. for at least two years.

3. A purified isozyme of SOD as claimed in claim 1 wherein the isozyme is extracted from the leaves of the Potentilla.

4. A formulation comprising the isozyme of SOD as claimed in claim 1 as an active ingredient.

5. A formulation comprising the isozyme of SOD as claimed in claim 4 further comprising at least one member of the group consisting of reduced glutathione, selenium, a source of selenium, a carrier, a flavoring agent and antioxidants.

6. A formulation as claimed in claim 5 wherein the source of selenium is selected from the group consisting of elemental selenium, selenomethionine and selenocysteine.

7. A formulation as claimed in claim 5 wherein the antioxidant is selected from the group consisting of vitamin C, vitamin E, alpha tocopherol, vitamin A, and beta carotene.

8. A formulation as claimed in claim 4 wherein the formulation is selected from the group consisting of solutions, lotions, creams, oils, gels, sticks, toothpick, sprays, ointments, balms, shampoo, serums, mousses, emollient, aerosol, roll-on, patches, lozenges, tablets, gums, dye compositions, pastes, and combinations thereof.

9. A formulation as claimed in claim 8 wherein the lozenge comprises a carrier that enables the lozenge to slowly dissolve in a user's mouth releasing said active ingredients in concentrations effective for reducing free radical damage.

10. A formulation as claimed in claim 4 further comprising at least one amino acid selected from the group consisting of cysteine, methionine, taurine, arginine, and zinc gluconate.

11. A formulation as claimed in claim 4 further comprising approximately 40 to 60% by weight of a gum composition.

12. A formulation as claimed in claim 11 wherein the gum composition is an elastomer, a polyvinyl acetate polymer, an acetylated monoglyceride, a wax with melting point below approximately 60° C., an elastomer solvent, a plasticizer or a filler.

13. A formulation as claimed in claim 4 further comprising a sweetener selected from the group consisting of xylitol, lactitol, sucrose, lactose and a saccharide.

14. A formulation as claimed in claim 4 further comprising at least one of 1–15% peroxidase, enzymatic substrate or peroxidase specific substrates.

15. A formulation as claimed in claim 14 wherein the peroxidase is selected from the group consisting of black radish peroxidase, horseradish peroxidase, lactoperoxidase, glutathione peroxidase and spinal cord peroxidase.

16. A formulation as claimed in claim 14 wherein the enzymatic substrate is selected from the group consisting of uric acid, glutathione, phenol, guaiacol, mesitol, 3,5-dichloro-2-hydroxybenzenesulfonic acid, aniline, dihydroxymaleic acid, cytochrome C, phenolphthalein, vitamin C, an iodide, a chloride, a bromide, 2–2'-azido-di-3-ethylbenzo-thiazoline-6-sulfonic acid, and $SCN^-$.

17. A formulation as claimed in claim 4 further comprising a lipophilic antioxidant in an effective antioxidizing amount, selected from the group consisting of tocopherol, tocopherol acetate, tocopherol linoleate, and tocopherol phosphate.

18. A formulation as claimed in claim 4 further comprising antioxidants, L-glutathione at 0.001% to 15% by weight, selenomethionine or selenium in a suitable carrier, wherein said formulation is suitable for topical application for the treatment of psoriasis, seborrhoeic dermatitis and related skin and scalp conditions.

19. A formulation as claimed in claim 18 further comprising at least zinc pyrithione, N-acetyl-L-cysteine, zinc oxide, vitamin E, or vitamin C.

20. A formulation as claimed in claim 18 capable of being encapsulated in protective membranes selected from the group consisting of liposomes, nanospheres and glycospheres.

21. A formulation as claimed in claim 18 dispersed or dissolved in at least one solvent selected from the group consisting of water, 1,2,4-butanetriol, propylene glycol, sorbitol esters, butylene glycol, polyethylene glycol, polypropylene glycol, glycerol, 1,2,6-hexanetriol, ethanol, isopropanol, butanediolmethanol, propanol, butanol, and ethylene glycol.

22. A formulation as claimed in claim 4, with or without melanin pigments, wherein the formulation is a cosmetic or pharmaceutical composition.

23. The formulation as claimed in claim 4, further comprising medium fatty acid glyceride, higher fatty acid glyceride, or both.

24. The formulation as claimed in claim 4, further comprising at least one member selected from the group consisting of mono-, di- and triglycerides of caprylic acid, capric acid, lauric acid, myristic acid, palmitic acid, oleic acid, linoleic acid, and linolenic acid.

25. The formulation as claimed in claim 4, further comprising liposomes, optionally mixed hyaluronic acid, at least one physiologically acceptable carrier, or mixed with both hyaluronic acid and at least one physiologically acceptable carrier, and wherein said formulation is a pharmaceutical composition.

26. A formulation as claimed in claim 6, further comprising at least one of steroids, non-steroidal anti-inflammatories, capsaicin extract, tissue respiratory factor or the local anesthetics of the caine family.

27. A formulation as claimed in claim 4, further comprising vitamin E, pyruvate, β-carotene, selenium, N-acetylcysteine, vitamin C, catalase, glutathione peroxidase, glutathione reductase, or alpha tocopherol alone or in combinations thereof.

28. A formulation comprising the isozyme of SOD as claimed in claim 1 together with a cosmetically acceptable peroxidase, cosmetically acceptable peroxidase substrate, solvents, carriers and additives.

29. A formulation as claimed in claim 28 made as a cosmetic emulsion further comprising at one member selected from the group consisting of steareth-2, steareth-21, propylene glycol-15 stearyl ether, cetearyl alcohol, butylene alcohol, water, a preservative, parabens, phenoxyethanol and tocopherol.

30. A formulation comprising the isozyme of SOD as claimed in claim 1 further comprising at least one substance selected from the group consisting of surfactants, colorants, perfumes, preserving agents, emulsifiers, synthetic oil, mineral oil, vegetable oil, fatty acids, fatty alcohols, a liquid carrier, water, fatty substances forming the fatty phase of an emulsion, milks creams, and resins, wherein the at least one substance is suitable for dermopharmaceutical purposes.

31. A formulation as claimed in claim 30 wherein the fatty phase of the emulsion is formed by employing compounds selected from the group consisting of mineral oils, vegetable oils, synthetic oils, waxes, fatty alcohols and fatty acids.

32. A formulation as claimed in claim 30 wherein the mineral oil is liquid paraffin.

33. A formulation as claimed in claim 30 wherein the synthetic oil is selected from the group consisting of ethyl palmitates, isopropyl palmitates, alkyl myristates, isopropyl myristate, butyl myristate, cetyl myristate, hexyl stearate, triglycerides of octanoic acids, triglycerides of decanoic acids, cetyl ricinoleate, stearyl octanoate, purcellin oil, and hydroxylated polyisobutene octanoate.

34. A formulation as claimed in claim 30 wherein the vegetable oil or wax is selected from the group consisting of sweet almond oil, avocado oil, coconut oil, wheat-germ oil, corn oil, castor oil, olive oil, palm oil, sesame oil, soya oil, argan oil, evening primrose oil, borage oil, essential oils, vegetable waxes, beeswax, synthetic waxes, and silicone waxes.

35. A formulation as claimed in claim 30 wherein the fatty alcohol is selected from the group consisting of cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol, erucyl alcohol and 2-octyl-dodecanol.

36. A formulation as claimed in claim 30 wherein the fatty acids are selected from the group consisting of stearic acid, myristic acid, palmitic acid, oleic acid, linoleic acid, lauric acid, isostearic acid, hydroxy-stearic acid, linolenic acid, ricinoleic acid, arachidic acid, behenic acid, erucic acid and lanolinic acids.

37. A formulation as claimed in claim 30 wherein the vegetable oil is selected from the group consisting of olive oil, maize oil, sesame oil, camellia oil, coconut oil and palm oil.

38. A formulation as claimed in claim 30 further comprising at least one amphiphilic agent, natural amphoteric surfactant, polyglycerin-fatty acid ester, polyoxyethylene-sorbitan fatty acid ester, sorbitan fatty acid ester or polyethylene glycol.

39. A formulation as claimed in claim 30 further comprising at least one amphoteric surfactant, soybean phospholipid, yolk lecithin, phosphatidyicholine, yolk lecithin, soybean lecithin, or phosphatidylethanolamine.

40. A formulation for topical application comprising an isozyme of a SOD as claimed in claim 1, wherein the formulation is in the form of a lotion, a serum, a liquid, semiliquid or milk emulsion wherein the emulsion is obtained by dispersing a fatty phase in an aqueous phase of oil-in-water or water-in-oil or suspensions, cream emulsions, gel emulsions, microgranulates, or vesicular dispersions that are ionic or nonionic.

41. A formulation as claimed in claim 40 further comprising at least one member selected from the group consisting of an antioxidant, vitamin E, alpha-d-tocopherol, alpha-dl-tocopherol, alpha-d-tocopherol acetate, alpha-dl-tocopherol acetate or alpha-d-tocopherol acid succinate, ascorbic acid, beta-carotene, polymer, mixture of polymers and selenium.

42. A formulation as claimed in claim 40 further comprising at least one member selected from the group consisting of an antioxidant, vitamin C, acetyl-L-carnitine and glutathione reductase.

43. A formulation as claimed in claim 40 further comprising free radical scavengers, antioxidants, anti-inflammatory agents, or a local anesthetic.

44. A formulation as claimed in claim 40 further comprising an agent selected from the group consisting of zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

45. A formulation as claimed in claim 40 further comprising an antioxidant together with the enzymes of the pentose monophosphate shunt pathway that regenerate reduced nicotinamide adenosine diphosphate (NADPH).

46. A formulation as claimed in claim 40, wherein said formulation is capable of being administered in at least one route selected from the group consisting of:
  (a) topical administration;
  (b) oral administration;
  (c) and parenteral administration.

47. A drug delivery system comprising the isozyme of SOD as claimed in claim 1 and a polymer, and optionally comprising an antioxidant within the matrix of the polymer, wherein the matrix does not interact with the antioxidant.

48. A drug delivery system as claimed in claim 47 wherein the drug delivery system comprises a natural, modified natural, synthetic, hydrophilic or hydrophobic polymer.

49. A drug delivery system as claimed in claim 47 wherein the polymer is selected from the group consisting of gelatin, hydrophilic polymers, hydrophobic polymers, ovalbumin, soybean proteins, gum Arabic, modified starch, methylcellulose, hydroxypropyl cellulose, and hydroxypropylmethyl.

50. A drug delivery system as claimed in claim 47 wherein the polymer is selected from the group consisting of polyamide, polyacrylate, polyurethane, waxes, polypropylene, and ethyl cellulose.

51. A drug delivery system as claimed in claim 47 adapted to dosage forms for local administration, ophthalmic administration, and transdermal administration.

52. A drug delivery system as claimed in claim 47 adapted to dosage forms for implants which will release the antioxidant in a controlled manner.

53. A drug delivery system as claimed in claim 47 made in the form of a film.

54. A drug delivery system as claimed in claim 53 wherein the film is prepared form ethanolic or chloroformic solutions of the polymers.

55. The formulation as claimed in 4, 28, 18, 22, 30, 40, or 47 that is in the from of a day cream, night cream, makeup removal cream, foundation cream, sun cream, fluid foundation, makeup removal milk, body protection or care milk, sun milk, lotion, gel, cleansing lotion, sun lotion, artificial tanning lotion, composition for the bath or a deodorizing composition wherein the formulation may further comprise a bactericidal agent.

56. The formulation as claimed in claims 4, 28, 18, 22, 30, 40, or 47 that is in the form of a shampoo that further comprises at least one member selected from the group consisting of melanin pigments, a cationic, anionic or non-ionic detergent, a dye, a composition for the reduction step of a deformation of hair, mercaptans, sulfites, and a composition for slowing down the loss of hair and for promoting fresh growth of hair, minoxidil (2,4-diamino-6-piperidino-3-pyrimidine oxide) and its derivatives, diazoxide (7-chloro-3-methyl-1,2,4-benzothiadiazine, 1,1-dioxide) and phenytoin (5,5-diphenyl imidazolidine-2,4-dione).

57. The formulation as claimed in claims 4, 28, 18, 22, 30, 40, or 47 that is in the form of an oral composition, a dental composition, or both an oral and dental composition, that further comprising at least one member selected from the group consisting of toothpaste, an adjuvant or additive for compositions for oral use, a surface-active agents, a thickening agent, a moisturizer, a polishing agent, silica, a fluoride, sodium fluoride, a sweetening agents and sodium saccharinate.

58. The formulation as claimed in claims 4, 28, 18, 22, 30, 40, or 47 further comprising an cosmetic compositions capable of maintaining the keratinous structure of the skin or of the hair.

59. An isozyme of SOD as claimed in claim 1, in a composition comprising an endogenous antioxidant, glutathione, an amino acid with selenium, selenemethionine or selenocysteine.

60. An isozyme of SOD as claimed in claim 1, that is in the form of a cream, lotion, solution, spray, aerosol, ointment, gel, balm, patch, or emulsion.

61. An isozyme of SOD as claimed in claim 1, further comprising an antioxidant, vitamin E, green tea or pycnogenols.

62. A toothpick comprising the isozyme of SOD as claimed in claim 1.

63. A pharmaceutical composition comprising the isozyme of SOD as claimed in claim 1, a pharmaceutically acceptable carrier and at least one therapeutic agent selected from the group consisting of antimicrobials, antibiotics, antioxidants, anti-plaque agents, analgesics, anti-tartar agents, anti-caries agents, hemostatic agents, anti-inflammatory agents, hormones, bleaching agents, vitamins, vaccines, caffeine and monoclonal antibodies.

64. An isozyme of SOD as claimed in claim 1, wherein the isozyme is capable of being immobilized onto a suitable medium selected from the group consisting of:

(a) a polymer matrix, a polymer film, wherein the polymer matrix or film are capable of being be used in biomedical/cosmetic/food science/field/industry as a scavenger of $O_2$;

(b) a water-soluble polysaccharide, dextran, dextrin;

(c) a protein, serum albumin, casein, amylases, trypsins; and (d) a synthetic polymer, polyethylene glycol, polyvinyl alcohol.

65. A purified isozyme of SOD as claimed in claim 1, wherein said enzyme has the following characteristics:

(d) $O_2^-$ scavenging activity at 25° C. for 30 days without adding any stabilizing agent polyols or sugars; and (e) stable at 4° C. for at least 8 months.

66. A method for identification of the target isozyme of claim 1 comprising (a) localizing various isozymes of SOD in the crude extract of the leaf on 7–12% native polyacrylamide gel;

(b) after electrophoresis, rinsing the gel with distilled water followed by incubation for 30 minutes in 2.5 mM NBT;

(c) immersing the gel in $1.17 \times 10^{-6}$ M riboflavin for 20 minutes and removed later onto a petri plate to expose to a light intensity of 25–1000$\mu$ Einstein/m$^2$/second using a fiber optic light source (Nikon) to develop purple color throughout the gel except for the locations where SOD was localized;

(d) incubating with nitroblue tetrazolium and riboflavin, and exposing to light at 4 different temperatures of –20, 4, 25 and 60° C.;

(e) when working at –20° C., adding glycerol (50% final concentration) in the incubation solution to avoid freezing;

(f) identifying the most prominent isozyme at all the temperatures for the purpose of purification.

67. A method for the preparation the isozyme of claim 1, comprising (a) homogenizing leaf tissue in a homogenizing buffer at pH 7.0–7.5 and at a temperature range between 4–8° C.;

(b) filtering the homogenate and centrifuging the filtrate at 8,000–13,000 rpm for 10–30 minutes at 4–8° C.;

(c) decanting the supernatant for purification of SOD;

(d) precipitating SOD with 30–60% ammonium sulfate;

(e) dissolving the precipitate in a 10 to 100 mM buffer at pH 7 to 7.5 and dialyzing for 18–36 hours with 6–12 changes of the buffer;

(f) loading the dialyzed protein onto a DEAE-Cellulose column and eluted with 100 to 500 ml of 100–500 mM KCl prepared in a buffer (all autoclaved or non-autoclaved);

(g) assaying fractions containing protein for SOD;

(h) fractionating SOD containing fractions on a high pressure liquid chromatography using 100–200 mM KCl1 prepared in 10–50 mM phosphate buffer (all autoclaved or non-autoclaved) with a flow rate of 0.8–1.0 ml per minute;

(i) assaying each peak was assayed for SOD activity SOD peak, obtained after HPLC and concentrating using a protein concentrator column;

(j) assaying concentrated protein for SOD activity at different temperatures ranging between −10 to +80° C. in the presence of glycerol to avoid freezing at sub-zero temperatures;

(k) localizing the purified SOD on 7 to 12% polyacrylamide gel by known methods;

(l) identifying the target isoenzyme by the method of claim 66; and (m) recovering the most prominent isoenzyme.

* * * * *